US009415033B2

(12) United States Patent
Ernst

(10) Patent No.: US 9,415,033 B2
(45) Date of Patent: Aug. 16, 2016

(54) ESTERS OF SHORT CHAINS FATTY ACIDS FOR USE IN THE TREATMENT OF IMMUNOGENIC DISORDERS

(71) Applicant: PROPONENT BIOTECH GMBH, Zug (CH)

(72) Inventor: Bettina Ernst, Zurich (CH)

(73) Assignee: PROPONENT BIOTECH GMBH, Zug (CH)

( * ) Notice: Subject to any disclaimer, the term of this patent is extended or adjusted under 35 U.S.C. 154(b) by 0 days.

(21) Appl. No.: 14/433,225

(22) PCT Filed: Oct. 3, 2013

(86) PCT No.: PCT/EP2013/070614
§ 371 (c)(1),
(2) Date: Apr. 2, 2015

(87) PCT Pub. No.: WO2014/053592
PCT Pub. Date: Apr. 10, 2014

(65) Prior Publication Data
US 2015/0246015 A1    Sep. 3, 2015

(30) Foreign Application Priority Data
Oct. 3, 2012 (EP) ..................... 12187074

(51) Int. Cl.
| A61K 31/22 | (2006.01) |
| A61K 9/00 | (2006.01) |
| A61K 31/19 | (2006.01) |
| A61K 31/192 | (2006.01) |
| A61K 31/215 | (2006.01) |
| A61K 31/222 | (2006.01) |
| A61K 31/25 | (2006.01) |

(52) U.S. Cl.
CPC .............. *A61K 31/22* (2013.01); *A61K 9/0043* (2013.01); *A61K 31/19* (2013.01); *A61K 31/192* (2013.01); *A61K 31/215* (2013.01); *A61K 31/222* (2013.01); *A61K 31/25* (2013.01); *A61K 9/006* (2013.01)

(58) Field of Classification Search
USPC ........................................................ 514/546
See application file for complete search history.

(56) References Cited

U.S. PATENT DOCUMENTS

| 4,735,967 A | 4/1988 | Neesby |
| 2011/0077300 A1 | 3/2011 | Ye et al. |

FOREIGN PATENT DOCUMENTS

| EP | 2030616 A1 | 3/2009 |
| JP | 2008195713 A1 | 8/2008 |
| WO | WO2008025837 A1 | 3/2008 |
| WO | WO2012131069 A1 | 10/2012 |

OTHER PUBLICATIONS

Cavaglieri, et al., "Differential Effects of Short-Chain Fatty Acids on Proliferation and Production of Pro- and Anti-Inflammatory Cytokines by Cultured Lymphocytes", Life Sciences, vol. 73, Jan. 1, 2003, pp. 1683-1690.
Fukuda, et al., "Immunomodulator e.g. for Treating Allergosis, Autoimmune Disease and Oral Infection Disease Comprises Acetic Acid and/or Propionic Acid as Active Ingredients", Thomson, vol. 2008, No. 79, Aug. 28, 2008, 3 pages.
Juneja, et al., "Mutagenicity of Nitrobenzyl Derivatives: Potential Bioreductive Anticancer Agents", Mutation Research, vol. 348, No. 3, 1995, pp. 137-145.
International Search Report for PCT/EP2013/070614 dated Feb. 11, 2014, 10 pages.
Meijer, et al., "Butyrate and Other Short-Chain Fatty Acids as Modulators of Immunity: What Relevance for Health?", Current Opinion in Clinical Nutrition and Metabolic Care, Nov. 2010, pp. 715-721.
Sherry, et al., "Sickness Behavior Induced by Endotoxin Can be Mitigated by the Dietary Soluble Fiber, Pectin, Through Up-Regulation of IL-4 and Th2 Polarization", Brain, Behavior and Immunity, vol. 24, No. 4, May 1, 2010, pp. 631-640.
Zhang, et al., "Valproic Acid Attenuates Inflammation in Experimental Autoimmune Neuritis", CMLS Cellular and Molecular Life Sciences, Oct. 27, 2008, pp. 4055-4065.

*Primary Examiner* — Kristin Vajda
(74) *Attorney, Agent, or Firm* — F. Brent Nix, Esq.; Johnson, Marcou & Isaacs, LLC

(57) ABSTRACT

The present invention relates to short chain fatty acids (SCFA) for use in transmucosal administration to a subject for the prevention, attenuation or treatment of a disease or disorder associated with a compromised Th1 immune response and/or an unwanted Th2 or Th2-like immune response by modulating a Th2 immune response towards a Th1 immune response, particularly for the treatment, prevention and/or amelioration of viral infections and as an adjuvant for promoting the efficiency of vaccines and/or prevention of allergic diseases or disorders.

11 Claims, 6 Drawing Sheets

Figure 1:
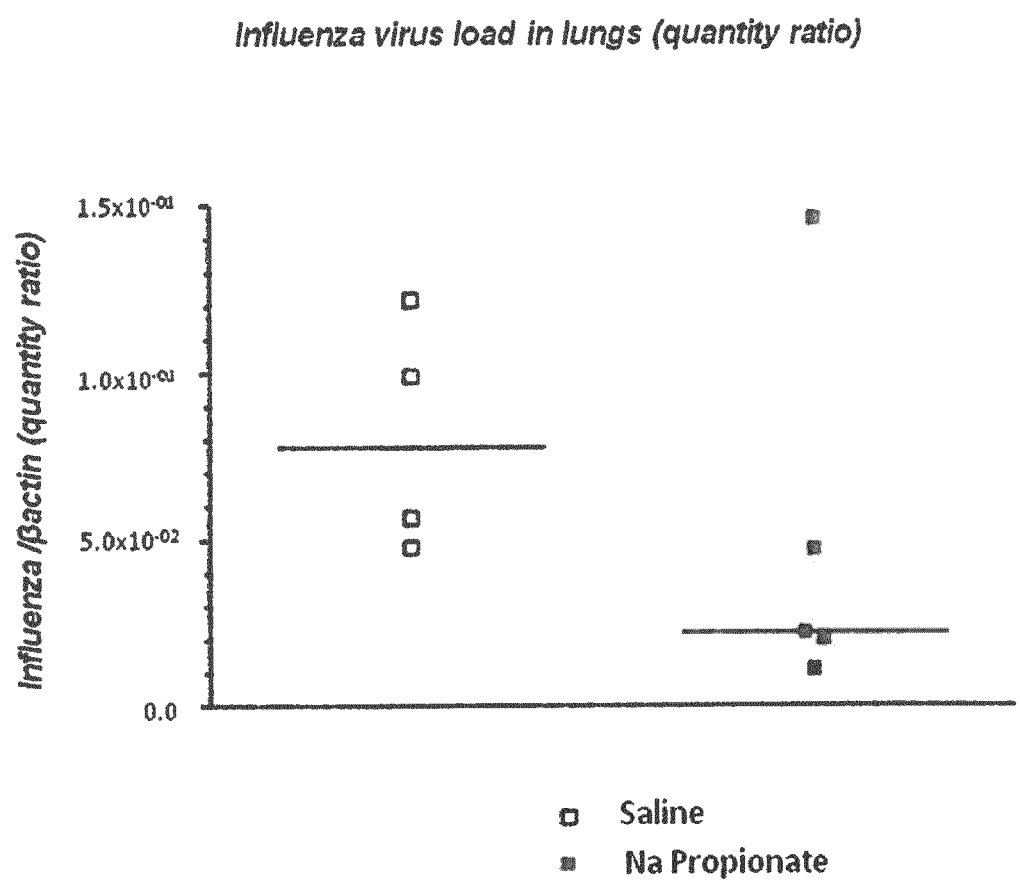

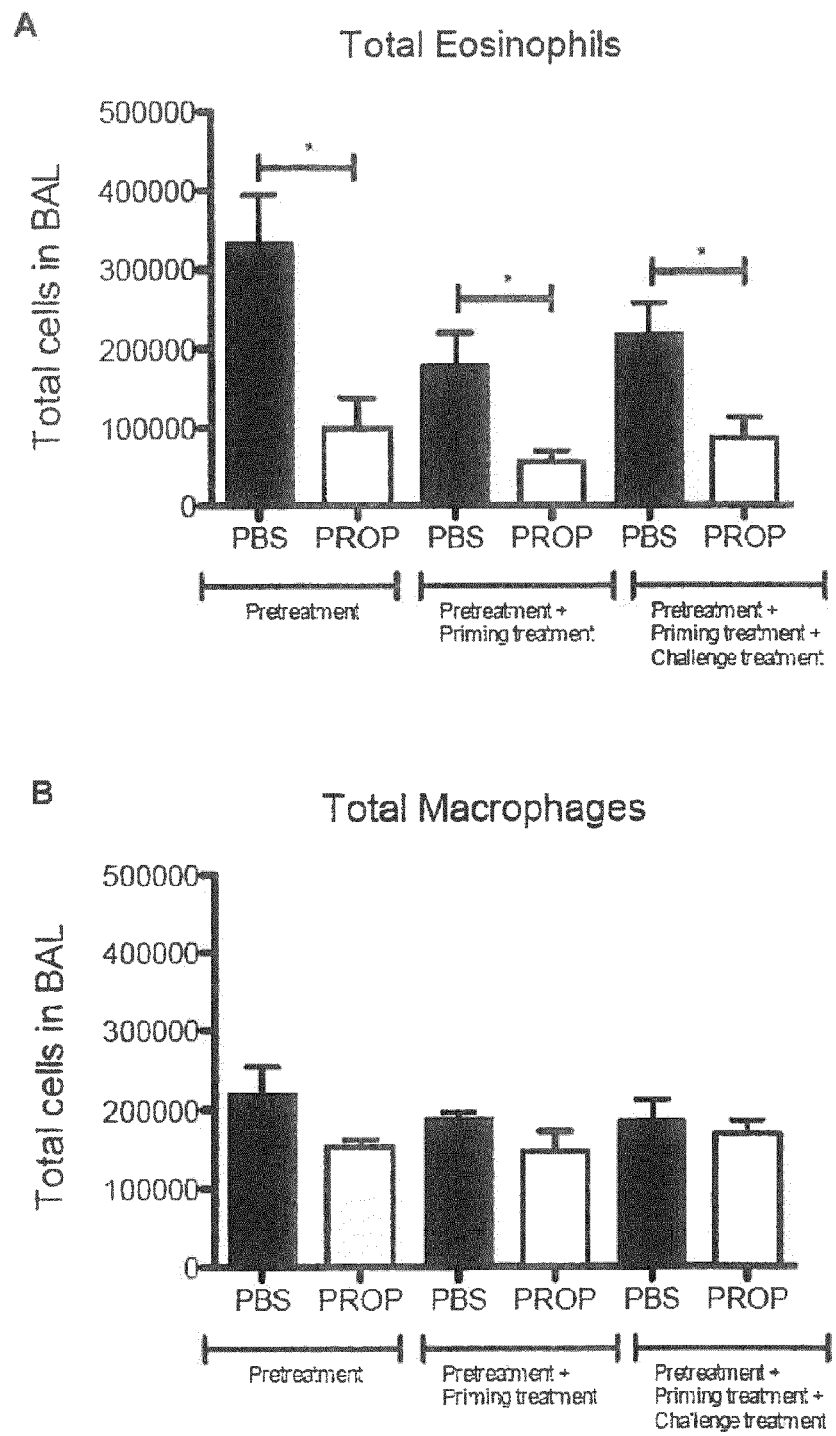
FIGURE 3A+B

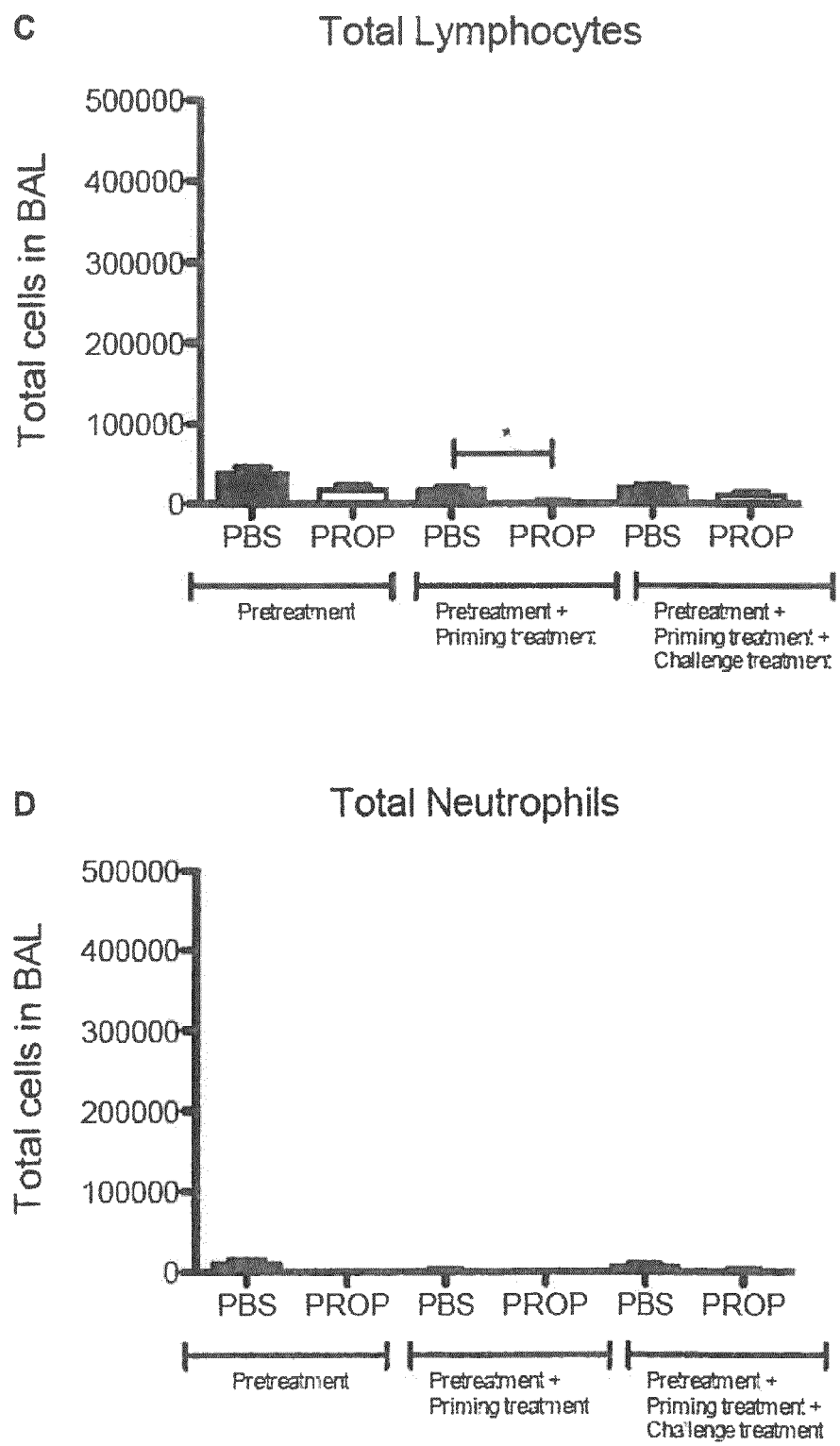
FIGURE 3C+D

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: Influenza matrix protein primer forward

<400> SEQUENCE: 1
ggactgcagc gtagacgctt                                               20

<210> SEQ ID NO 2
<211> LENGTH: 24
<212> TYPE: DNA
<213> ORGANISM: Artificial sequence
<220> FEATURE:
<223> OTHER INFORMATION: Influenza matrix protein primer reverse

<400> SEQUENCE: 2
catcctgttg tatatgaggc ccat                                          24

<210> SEQ ID NO 3
<211> LENGTH: 21
<212> TYPE: DNA
<213> ORGANISM: Artificial sequence
<220> FEATURE:
<223> OTHER INFORMATION: B-actin primer forward

<400> SEQUENCE: 3
ccctgaagta ccccattgaa c                                             21

<210> SEQ ID NO 4
<211> LENGTH: 20
<212> TYPE: DNA
<213> ORGANISM: Artificial sequence
<220> FEATURE:
<223> OTHER INFORMATION: B-actin primer reverse

<400> SEQUENCE: 4
cttttcacgg ttggccttag                                               20

<210> SEQ ID NO 5
<211> LENGTH: 23
<212> TYPE: DNA
<213> ORGANISM: Artificial sequence
<220> FEATURE:
<223> OTHER INFORMATION: MPV-specific primer forward

<400> SEQUENCE: 5
gccgttagct tcagtcaatt caa                                           23
```

```
<210> SEQ ID NO 6
<211> LENGTH: 22
<212> TYPE: DNA
<213> ORGANISM: Artificial sequence
<220> FEATURE:
<223> OTHER INFORMATION: MPV-specific primer reverse

<400> SEQUENCE: 6
tccagcattg tctgaaaatt gc                                              22

<210> SEQ ID NO 7
<211> LENGTH: 20
<212> TYPE: DNA
<213> ORGANISM: Artificial sequence
<220> FEATURE:
<223> OTHER INFORMATION: GAPDH forward

<400> SEQUENCE: 7
gggtgtgaac cacgagaaat                                                 20

<210> SEQ ID NO 8
<211> LENGTH: 20
<212> TYPE: DNA
<213> ORGANISM: Artificial sequence
<220> FEATURE:
<223> OTHER INFORMATION: GAPDH reverse

<400> SEQUENCE: 8
ccttccacaa tgccaaagtt                                                 20

<210> SEQ ID NO 9
<211> LENGTH: 20
<212> TYPE: DNA
<213> ORGANISM: Artificial sequence
<220> FEATURE:
<223> OTHER INFORMATION: Influenza matrix protein forward

<400> SEQUENCE: 9
ggactgcagc gtagacgctt                                                 20

<210> SEQ ID NO 10
<211> LENGTH: 24
<212> TYPE: DNA
<213> ORGANISM: Artificial sequence
<220> FEATURE:
<223> OTHER INFORMATION: Influenza matrix protein reverse

<400> SEQUENCE: 10
catcctgttg tatatgaggc ccat                                            24
```

ESTERS OF SHORT CHAINS FATTY ACIDS FOR USE IN THE TREATMENT OF IMMUNOGENIC DISORDERS

CROSS REFERENCE TO RELATED APPLICATIONS

This application is a 35 U.S.C. §371 national stage application of International Application No. PCT/EP2013/70614 filed on Oct. 3,2013, published in English under PCT Article 21(2), which claims the benefit of priority to European Patent Application No. 12187074.5 filed on Oct. 3, 2012, the disclosures of which are hereby incorporated by reference.

The present invention relates to short chain fatty acids (SCFA) for modulating an immune response. In particular, compositions and methods are provided for use in the treatment, prevention or attenuation of viral infections and/or virus-induced exacerbations of allergy or autoimmunity. In a second aspect, compositions and methods are provided for use in the prevention of development of a Th2 induced inflammatory condition in a tissue or organ of a subject.

Inefficient or misdirected immune responses are responsible for a broad range of human diseases and disorders. It is commonly accepted that an inappropriate Th1 cell driven immune response can be the reason for insufficient virus clearing and the development of autoimmune and allergic diseases or disorders.

Furthermore, cytokine compositions play also an important role in the chronic inflammation of allergic diseases such as, for example, asthma and play a critical role in orchestrating the allergic inflammatory response. Of particular importance to allergic disease is the recent recognition of the regulation of helper immune function by two lineages of T helper cells, i.e., Th1 and Th2, by these cytokines. The Th2 hypothesis of allergy considers atopy as a Th2-driven hypersensitivity reaction to allergens of complex genetic and environmental origins, in which the Th1 lineage, normally driven by IL-2, TNF, and IFN-γ is deficient, and in which a predominant Th2 response is seen that is mediated by IL-4, IL-13, IL-5, and IL-10.

Literature shows that Th2 lymphocytes are presently considered the main orchestrator of allergic airway inflammation underlying asthma. Functional analysis of the role of cytokines, largely based on in vivo animal models, confirms this hypothesis. During T cell differentiation from naive T cells into Th1 and Th2 cells, the expression of IL-10 in Th1 cells slowly disappear, whereas Th2 cells produce more IL-10. In contrast, Th2 cells secrete IL-4, IL-5, IL-9, IL-10, and IL-13, which are involved in isotype switching of B cells as well as proliferation and differentiation into antibody-secreting plasma cells. Interleukin-4 and IL-10 are also regulatory cytokines, antagonizing the activities of Th1 cytokines. Thus, the nature, intensity and duration of a specific immune response depend on the delicate balance between Th1 and Th2 numbers or activities (or both).

In particular, IL-4 and IL-13 are involved in the isotype switch from IgM to IgE, the antibody responsible for classic allergy and implicated in the pathophysiology of allergic asthma. Excessive IL-4 production by Th2 cells has been associated with elevated IgE production and allergy.

Recent studies with gene knockout mice have demonstrated that T helper 2 (Th2) cell-derived cytokines, including IL-4, IL-5, and IL-13, play important roles in causing allergic airway inflammation. In vitro, IL-4 is necessary for differentiation of the naive CD-positive T-cells within the Th2 subpopulation secreting IL-4, IL-5, IL-6, IL-10 and IL-13. Although IL-4 induces IgE synthesis and enables the immediate type of hypersensitivity reaction, there is certain evidence suggesting in vitro and in vivo anti-inflammatory effects of IL-4. IL-4 is critical in switching B lymphocytes to produce IgE, for expression of VCAM-1 on endothelial cells, and for inducing the differentiation of Th2 cells and IL-5, which is essential for the differentiation of eosinophils.

The critical role of IL-5 in eosinophilia has been confirmed by the use of an anti-IL-5 antibody in asthmatic patients, which almost depletes circulating eosinophils and prevents eosinophil recruitment into the airway after allergen. IL-5 is a cytokine that is not encountered at high levels in healthy individuals. The control of IL-5 protein production takes place at the level of transcription. IL-10 is a potent anti-inflammatory cytokine that inhibits the synthesis of many inflammatory proteins, including cytokines (TNF-α, granulocyte macrophage colony stimulating factor, IL-5, chemokines) and inflammatory enzymes (inducible nitric oxide synthase) that are over-expressed in asthma. In addition, IL-10 inhibits antigen presentation and sensitisation. IL-13 signals through the IL-4 receptor α-chain, but may also activate different intracellular pathways.

Thus, IL-4, IL-5 and IL-10 are of critical importance in the differentiation of Th2 cells and are therefore 'upstream' cytokines that are an attractive therapeutic target in the treatment of atopic diseases.

In addition to Th2 cytokines, IgE-dependent activation of mast cells has been suggested to play a role in allergic airway inflammation. Whereas IgE cross-linking by antigens did not induce eosinophil recruitment into the airways or airway hyperreactivity, IgE cross-linking induced T cell recruitment into the airways. In addition, when antigen-specific Th2 cells were transferred to IgE transgenic mice, IgE cross-linking significantly enhanced antigen-induced eosinophil recruitment into the airways. These findings suggest that IgE-dependent mast cell activation plays an important role in allergic airway inflammation by recruiting Th2 cells into the site of allergic inflammation.

Eosinophils are believed to be the final effector cells in the pathogenesis of allergic disease and bronchial asthma. These cells also have the capacity to synthesize and release a wide array of cytokines. Eosinophils can also secrete TGF-α and TGF-β and as such may account for the eosinophil-derived stimulatory capacity for fibroblast proliferation, which leads to changes in the lung architecture and thus may contribute to the irreversibility of bronchial asthma. Likewise, human eosinophils synthesize and secrete IL-6, which facilitates IL-4 dependent IgE production (Coyle and Tsuyuki, 1995).

The IL-4 cytokine released from Th2 and Th2-like cells is likely to be central to the pathophysiology of asthma and allergy in that it contributes to aberrant IgE production, eosinophilia and, perhaps, mucosal susceptibility to viral infections. Accordingly, it was suggested in Coyle and Tsuyuki (1995) that inhibitors of Th2 cytokine production will prove to be of therapeutic value. It was further suggested that inhibition of IL-4 may offer advantages in steroid resistant asthma by preventing/reversing impaired steroid receptor function and in viral mediated exacerbations of asthma, where IL-4 may be of central importance in switching cytotoxic CD8+ T cells to a Th2 like phenotype.

Viral infections are a major cause of worldwide morbidity and mortality. Acute and chronic viral infections cause direct pathology, but they can also influence other concurrent responses (e.g. exacerbations of allergy of allergic diseases or autoimmunity) or in fact shape the immune system in such a way that subsequent immune responses develop differently. Important examples are virally conferred protection or enhancement of allergy subsequent to infection, or the development of immunodeficiency in chronic infection.

For example, Respiratory-Syncytial-Virus (RSV) is a major respiratory pathogen that infects nearly all children by the age of 2 or 3; however, natural infection results in poor immunity and consequently people are not protected against subsequent infection. Severe prior infection with RSV has been linked with an increased susceptibility to the development of asthma although the molecular mechanisms remain to be fully elucidated. In addition, akin to Influenza virus infection, following RSV infection there is an increased susceptibility to bacterial infections and consequently impaired anti-bacterial responses. There are currently no vaccines available for RSV and prophylactic treatment with monoclonal antibodies are the primary source of protection for infants and the elderly.

It remains unclear how RSV manages to subvert protective immunity, and the mechanisms by which infection may predispose people to asthma remains highly debated. However, a tragic vaccine trial failure provided some key insight into the pathogenic mechanisms: young children vaccinated with formalin inactivated RSV developed a profound Th2-based immune response upon subsequent natural infection by RSV, which in some cases was fatal.

It is known that pathogens such as viruses activate CD8+ T cells. These cells typically produce a Th1 like cytokine panel (INF-γ, IL-2) after in vitro stimulation. CD8+ T cells are further known to mediate lysis of viral infected cells and inhibition of viral replication through the production of IFN-γ.

However, it has recently been shown that viral antigen-specific activation of CD8+ T cells in the presence of IL-4 may lead to a switch of CD8+ T cells towards a Th2 like phenotype that produces IL-5 and reduced amounts of IFN-γ. This phenotype switch may contribute to an exacerbation of asthma severity due to IL-5 production. Further, the reduced secretion of IFN-γ may impair the normal host response, leading to delayed viral clearance from the lung. (Coyle and Tsuyuki (1995)).

Further viral infections leading to a worldwide morbidity and mortality are caused by influenza viruses and require seasonal vaccination.

Even though vaccines against viral infections can be very effective, there is a clear need for improvements in terms of vaccine design and increased adjuvant efficiency to promote vaccine action. In particular, the possibility of utilizing an adjuvant which required less vaccine to elicit protection against infection would be high valuable especially during viral pandemics.

Accordingly, there is a desperate need for improved strategies for treating viral infections such as RSV and Influenza, and/or for preventing or ameliorating autoimmune diseases, allergic disorders/diseases.

This need could be satisfied within the scope of the present invention by providing compositions and methods for the modulation of a Th2 or Th2-like immune response towards a Th1 immune response, which leads to prevention or attenuation of viral infections and/or virus-induced exacerbations of allergy or autoimmunity and of allergic disorders in general.

In particular, it was surprisingly found within the scope of the present invention that short chain fatty acids as disclosed and claimed herein can be used in human therapy for use in the treatment, prevention or attenuation of viral infections and/or virus-induced exacerbations of allergy or autoimmunity and the treatment, prevention or attenuation of allergic disorders in general upon transrnucosal, particularly intranasal, particularly sublingual administration of the short chain fatty acids.

The present invention thus provides a compound of formula (I)

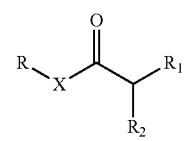

(I)

wherein
X represents —O—, —S—, or —NH—, preferably —O—;
R represents hydrogen, alkyl, aryl, arylalkyl, polyalkylene glycol;
$R_1$ represents hydrogen, alkyl, hydroxyalkyl, arylalkylcarboxylic acid;
$R_2$ represents hydrogen, alkyl, —O—$R_3$; and
$R_3$ represents hydrogen, aryl, arylalkyl, hydroxyalkyl-carboxyl;
or pharmaceutically acceptable salts thereof, for modulation of a Th2 or Th2-like immune response towards a Th1 immune response upon transmucosal administration, particularly upon intranasal, particularly upon sublingual administration, to a subject.

In one embodiment, the present invention relates to a compound of formula (I)

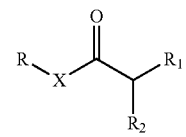

(I)

wherein
X represents —O—, —S—, or —NH—, preferably —O—;
R represents hydrogen, alkyl, aryl, arylalkyl, polyalkylene glycol;
$R_1$ represents hydrogen, alkyl, hydroxyalkyl, arylalkylcarboxylic acid;
$R_2$ represents hydrogen, alkyl, —O—$R_3$; and
$R_3$ represents hydrogen, aryl, arylalkyl, hydroxyalkyl-carboxyl;
or pharmaceutically acceptable salts thereof for use in transmucosal administration to a subject for the prevention, attenuation or treatment of a disease or disorder associated with a compromised Th1 immune response and/or an unwanted Th2 or Th2-like immune response.

This may be achieved by modulation of a Th2 or Th2-like immune response towards a Th1 immune response In one embodiment, the present invention relates to a compound of formula (I)

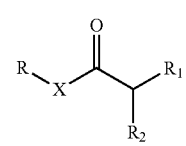

(I)

wherein
X represents —O—, —S—, or —NH—, preferably —O—;

R represents hydrogen, alkyl, aryl, arylalkyl, polyalkylene glycol;

$R_1$ represents hydrogen, alkyl, hydroxyalkyl, arylalkylcarboxylic acid;

$R_2$ represents hydrogen, alkyl, —O—$R_3$; and $R_3$ represents hydrogen, aryl, arylalkyl, hydroxyalkyl-carboxyl;

or pharmaceutically acceptable salts thereof, for use in the treatment, prevention or attenuation of viral infections and/or virus-induced exacerbations of allergy or autoimmunity and/or allergic diseases and disorders upon transmucosal administration, particularly upon intranasal, particularly upon sublingual administration, to a subject.

The compound of formula (I) may also be used as an adjuvant for inducing, promoting or enhancing an immune response in a subject treated with an immunogen, for example, an immunogen comprised in a vaccine, particularly a viral vaccine.

In one embodiment, the compound of formula (I) is a compound, wherein

X represents —O—, —S—, or —NH—, preferably —O—;

R represents hydrogen, alkyl, aryl, arylalkyl, polyalkylene glycol;

$R_1$ represents hydrogen, alkyl, hydroxyalkylcarboxylic acid;

$R_2$ represents hydrogen, alkyl, —O—$R_3$; and $R_3$ represents hydrogen, aryl, arylalkyl, hydroxyalkyl-carboxyl;

or pharmaceutically acceptable salts thereof.

In a specific embodiment the compound of formula (I) is a compound according to the invention and as described herein in the various embodiments, wherein X represents —O—, —S—, or —NH—, preferably —O—;

R represents hydrogen, $C_1$-$C_6$ alkyl, unsubstituted or substituted phenyl with one or more, same or different, substituents selected from the group consisting of nitro, halogen, amino, hydroxyl, cyano, $C_1$-$C_4$ alkyloxy or trifluoro;

$R_1$ represents hydrogencarboxylic acid, $C_1$-$C_6$ alkyl, hydroxy-$C_1$-$C_6$ alkyl wherein the alkyl group may be unsubstituted or substituted with one or more, same or different, substituents selected from the group consisting of hydroxyl, amino, carboxylic acid, halogen, cyano, or nitro;

$R_2$ represents hydrogen, $C_1$-$C_6$ alkyl, —O—$R_3$; and $R_3$ represents hydrogen, unsubstituted or substituted phenyl with one or more, same or different, substituents selected from the group consisting of nitro, halogen, amino, hydroxyl, cyano, $C_1$-$C_4$ alkyloxy or trifluoro, phenyl-$C_1$-$C_6$ alkyl wherein the phenyl group may be unsubstituted or substituted with one or more, same or different, substituents selected from the group consisting of nitro, halogen, amino, hydroxyl, cyano, $C_1$-$C_4$ alkyloxy or trifluoro, hydroxy-$C_1$-$C_6$ alkyl-carboxyl;

or pharmaceutically acceptable salts thereof.

In another specific embodiment, the compound of formula (I) is a compound according to the invention and as described herein in the various embodiments, wherein X is —O—, R is hydrogen;

$R_1$ represents hydrogencarboxylic acid, $C_1$-$C_4$ alkyl, hydroxy-$C_1$-$C_4$ alkyl wherein the alkyl group may be unsubstituted or substituted with one or more, same or different, substituents selected from the group consisting of hydroxyl, amino, or carboxylic acid, preferably hydroxyl and/or carboxylic acid; and $R_2$ is hydrogen or $C_1$-$C_4$ alkyl;

or pharmaceutically acceptable salts thereof.

In another specific embodiment, the compound of formula (I) is a compound according to the invention and as described herein in the various embodiments, wherein X is —O—, R is hydrogen;

$R_1$ represents hydrogencarboxylic acid, $C_1$-$C_4$ alkyl, hydroxy-$C_1$-$C_4$ alkyl wherein the alkyl group may be unsubstituted or substituted with one or more, same or different, substituents selected from the group consisting of hydroxyl, amino or carboxylic acid, preferably hydroxyl and/or carboxylic acid; and $R_2$ is —O$R_3$; and $R_3$ represents hydrogen, unsubstituted or substituted phenyl with one or more, same or different, substituents selected from the group consisting of nitro, halogen, amino, hydroxyl, cyano or methoxy, phenyl-$C_1$-$C_4$ alkyl wherein the phenyl group may be unsubstituted or substituted with one or more, same or different substituents selected from the group consisting of nitro, halogen, amino, hydroxyl, cyano or methoxy, hydroxy-$C_1$-$C_3$ alkyl-carboxyl;

or pharmaceutically acceptable salts thereof.

In another specific embodiment, the compound of formula (I) is a compound according to the invention and as described herein in the various embodiments, wherein X is —O—, R is hydrogen;

$R_1$ represents hydrogencarboxylic acid, $C_1$-$C_3$ alkyl, hydroxy-$C_1$-$C_3$ alkyl wherein the alkyl group may be unsubstituted or substituted with one or more, same or different, substituents selected from the group consisting of hydroxyl and/or carboxylic acid; and $R_2$ is hydrogen or $C_1$-$C_4$ alkyl;

or pharmaceutically acceptable salts thereof.

In another specific embodiment, the compound of formula (I) is a compound according to the invention and as described herein in the various embodiments, wherein X is —O—, R is hydrogen;

$R_1$ represents hydrogen, carboxylic acid, $C_1$-$C_3$ alkyl, hydroxy-$C_1$-$C_3$ alkyl wherein the alkyl group may be unsubstituted or substituted with one or more, same or different, substituents selected from the group consisting of hydroxyl or carboxylic acid;

$R_2$ is —O$R_3$; and $R_3$ represents hydrogen, unsubstituted or substituted phenyl with one or more, same or different, substituents selected from the group consisting of nitro, halogen, amino, hydroxyl, cyano or methoxy, phenyl-$C_1$-$C_4$ alkyl wherein the phenyl group may be unsubstituted or substituted with one or more, same or different, substituents selected from the group consisting of nitro, halogen, amino, hydroxyl, cyano, or methoxy, hydroxy-$C_1$-$C_3$ alkyl-carboxyl;

or pharmaceutically acceptable salts thereof.

In particular, the compound of formula (I) is a compound according to the invention and as described herein in the various embodiments, wherein X is —O—, R is hydrogen;

$R_1$ is selected from the group consisting of hydrogen, methyl, ethyl, n-propyl, isopropyl, hydroxymethyl, dihydroxymethyl, hydroxyethyldicarboxylic acid, carboxylic acidmethylcarboxylic acid, hydroxymethylcarboxylic, ethylcarboxylic acid; and $R_2$ is selected from the group consisting of hydrogen, hydroxyl or methyl;

or pharmaceutically acceptable salts thereof, or wherein

X is —O—,

R is hydrogen;

$R_1$ is selected from the group consisting of hydrogen, methyl, ethyl, n-propyl, isopropyl;

$R_2$ is —$OR_3$; and $R_3$ is selected from the group consisting of 1-hydroxyethylcarbonyl, benzyl, nitrophenyl;

or pharmaceutically acceptable salts thereof.

In yet another specific embodiment, the compound of formula (I) is a compound according to the invention and as described herein in the various embodiments, wherein X is —O—, R represents $C_1$-$C_4$ alkyl, unsubstituted or substituted phenyl with one or more, same or different, substituents selected from the group consisting of nitro, halogen, amino, hydroxyl, cyano or methoxy, phenyl-$C_1$-$C_4$ alkyl wherein the phenyl group may be unsubstituted or substituted with one or more, same or different, substituents selected from the group consisting of halogen, nitro, amino, hydroxyl, cyano or methoxy, polyalkylene glycol;

$R_1$ is carboxylic acid, $C_1$-$C_4$ alkyl or hydroxy-$C_1$-$C_4$ alkyl, wherein the alkyl group may be unsubstituted or substituted with one or more, same or different, substituents selected from the group consisting of hydroxyl, amino or carboxylic acid; and $R_2$ is hydrogen;

or pharmaceutically acceptable salts thereof.

In yet another specific embodiment, the compound of formula (I) is a compound according to the invention and as described herein in the various embodiments, wherein X is —O—, R represents $C_1$-$C_4$ alkyl, unsubstituted or substituted phenyl with one or more, same or different, substituents selected from the group consisting of nitro, halogen, amino, hydroxyl, cyano or methoxy, phenyl-$C_1$-$C_4$ alkyl wherein the phenyl group may be unsubstituted or substituted with one or more, same or different, substituents selected from the group consisting of halogen, nitro, amino, hydroxyl, cyano or methoxy, polyalkylene glycol;

$R_1$ is carboxylic acid, $C_1$-$C_3$ alkyl or hydroxy-$C_1$-$C_3$ alkyl wherein the alkyl group may be unsubstituted or substituted with one or more, same or different, substituents selected from the group consisting of hydroxyl and/or carboxylic acid; and $R_2$ is hydrogen;

or pharmaceutically acceptable salts thereof.

In particular, the present invention thus provides a compound of formula (I)

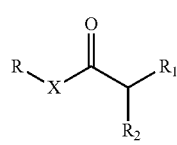

(I)

wherein

X is —O—,

R is selected from the group consisting of methyl, ethyl, propyl, benzyl, nitrobenzyl, polyethylene glycol;

$R_1$ selected from the group consisting of ethyl, hydroxyethyl, methyl, hydroxymethyl; and $R_2$ is hydrogen;

or pharmaceutically acceptable salts thereof for modulation of a Th2 or Th2-like immune response towards a Th1 immune response upon transmucosal administration, particularly upon intranasal, particularly upon sublingual administration, to a subject.

The present invention further provides a compound of formula (I)

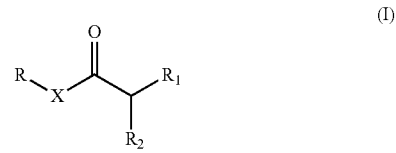

(I)

wherein

X is —O—,

R is selected from the group consisting of methyl, ethyl, propyl, benzyl, nitrobenzyl, polyethylene glycol;

$R_1$ selected from the group consisting of ethyl, hydroxyethyl, methyl, hydroxymethyl; and $R_2$ is hydrogen;

or pharmaceutically acceptable salts thereof for use in the treatment, prevention or attenuation of viral infections and/or virus-induced exacerbations of allergy or autoimmunity upon transmucosal administration, particularly upon intranasal, particularly upon sublingual administration, to a subject.

In particular, the compound of formula (I) may also be used as an adjuvant for inducing, promoting or enhancing an immune response in a subject treated with an immunogen, for example, an immunogen comprised in a vaccine, particularly a viral vaccine.

In a specific embodiment, the compound of formula (I) is a compound according to the invention and as described herein in the various embodiments selected from the group consisting of propionic acid, acetic acid, butyric acid, isobutyric acid, 2-hydroxyproirinic acid, dilactic acid, 2-benzyloxypropionic acid, 2-(p-nitrophenyl)-oxy-propionic acid, 3-hydroxypropionic acid, 2,3-dihydroxypropionic acid, methyl 3-hydroxypropionate, ethyl 3-hydroxypropionate, propyl 3-hydroxypropionate, benzyl 3-hydroxypropionate, para-nitrophenyl 3-hydroxypropionate, p-nitrobenzyl 3-hydroxypropionate, polyethylene glycol 3-hydroxypropionate, methyl propionate, ethyl propionate, propyl propionate, benzyl propionate, p-nitrophenyl propionate, p-nitrobenzyl propionate, 2-(4-Isobutylphenyl) propionic acid, lactic acid, citric acid, malic acid, malonic acid, succinic acid, and tartaric acid; or pharmaceutically acceptable salts thereof.

In still another embodiment of the invention, the compound of formula (I) of the invention as described herein in the various embodiments is selected from the group consisting of isobutyric acid, 3-hydroxypropionic acid, 2,3-dihydroxypropionic acid, lactic acid, or citric acid, or pharmaceutically acceptable salts thereof.

In particular, the compound of formula (I) is propionic acid or a pharmaceutically acceptable salt thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention.

The compounds of this invention may also contain linkages (e.g., carbon-carbon bonds) wherein bond rotation is restricted about that particular linkage, e.g. restriction resulting from the presence of a ring or double bond. Accordingly, all cis-trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of formula (I) of the invention as described herein in the various embodiments, but particularly propionic acid, or a pharmaceutically acceptable salt thereof, or a composition comprising the SCFA compound of formula (I) according to the invention and as described herein, but particularly propionic acid, or a pharmaceutically acceptable salt thereof, particularly in a therapeutically effective amount, optionally, together with a pharmaceutically acceptable carrier and/or a balanced salt solution as disclosed herein, is used for transmucosal administration, particularly for sublingual administration, particularly for intranasal administration to a subject for the treatment, prevention or attenuation of viral infections and/or virus-induced exacerbations of allergy or autoimmunity and/or allergic diseases and disorders.

The compounds of formula (I) of the invention as described herein in the various embodiments, but particularly propionic acid, or a pharmaceutically acceptable salt thereof, or a composition comprising the SCFA compound of formula (I) according to the invention and as described herein, but particularly propionic acid, or a pharmaceutically acceptable salt thereof, particularly in a therapeutically effective amount, optionally, together with a pharmaceutically acceptable carrier and/or a balanced salt solution as disclosed herein, may also be used upon transmucosal administration, particularly upon sublingual, particularly upon intranasal administration, as an adjuvant for inducing, promoting or enhancing an immune response in a subject treated with an immunogen, for example, an immunogen comprised in a vaccine, particularly a viral vaccine.

In one embodiment, transmucosal administration, particularly sublingual, particularly intranasal administration, of a single or repetitive dose of said SCFA compound of formula (I) or a pharmaceutically acceptable salt thereof, or a composition comprising the SCFA compound of formula (I) according to the invention and as described herein, or a pharmaceutically acceptable salt thereof, optionally, together with a pharmaceutically acceptable carrier, and/or a balanced salt solution as disclosed herein, said SCFA compound or composition leads to a reduction of the virus titer in a treated subject, which is up to 5-fold, particularly up to 10-fold, particularly up to 25-fold, particularly up to 50-fold, particularly up to 100-fold, particularly up to 200-fold, particularly up to 500-fold, particularly up to 1000-fold, particularly up to 2500-fold, particularly up to 5000-fold, particularly up to 10000-fold more effective as compared to systemic administration, such as for instance oral or intraperitoneal administration.

In certain embodiments, the present invention relates to a SCFA compound of formula (I) according to the invention and as described herein or to a pharmaceutically acceptable salt thereof, or to a composition comprising the SCFA compound of formula (I) according to the invention and as described herein, or a pharmaceutically acceptable salt thereof, particularly in a therapeutically effective amount, optionally, together with a pharmaceutically acceptable carrier, and/or a balanced salt solution as disclosed herein, for use in a method for inducing antigen-specific T cells in a subject, particularly of antigen-specific CD4+ T cells or CD8+ T cells or both, wherein said SCFA compound of formula (I) or a composition comprising the SCFA compound of formula (I) according to the invention and as described herein is administered to a subject in need thereof transmucosally, particularly intranasally, particularly sublingually.

The SCFA compound of formula (I) according to the invention and as described herein is, in a specific embodiment, propionic acid or a pharmaceutically acceptable salt thereof.

In one aspect of the invention, the CD8+ T cells are memory CD8+ T cells.

In another aspect of the invention, said antigen-specific T cells are induced in the airways, particularly in the lung of the subject.

In one embodiment, the SCFA compound of formula (I) or a composition comprising the SCFA compound of formula (I) according to the invention and as described herein in the various embodiments, optionally together with a balanced salt solution as disclosed herein, is used for transmucosal administration, particularly for sublingual, particularly for intranasal administration to a subject for prevention, alleviation or treatment of a viral infection, particularly a viral infection in the airways of a subject.

In a specific embodiment, said SCFA compound of formula (I) according to the invention and as described herein is propionic acid or a pharmaceutically acceptable salt thereof.

In one embodiment, the SCFA compound of formula (I) or a composition comprising the SCFA compound of formula (I) according to the invention and as described herein in the various embodiments, particularly a propionic acid or a pharmaceutically acceptable salt thereof, or a composition comprising propionic acid or a pharmaceutically acceptable salt thereof, optionally together with a balanced salt solution as disclosed herein, is used for transmucosal administration, particularly for sublingual, particularly for intranasal administration to a subject for prevention, alleviation or treatment of a viral infection, particularly a viral infection in the airways of a subject Accordingly, in one embodiment, the present invention relates to a SCFA compound of formula (I) according to the invention and as described herein in the various embodiments or to a pharmaceutically acceptable salt thereof, or to a composition comprising the SCFA compound of formula (I) according to the invention and as described herein, or a pharmaceutically acceptable salt thereof, particularly in a therapeutically effective amount, optionally, together with a pharmaceutically acceptable carrier and/or a balanced salt solution as disclosed herein, for use in transmucosal administration, particularly in sublingual, particularly in intranasal administration to a subject for prevention, alleviation or treatment of a viral infection, particularly a viral infection in the airways of a subject, such as asthma, chronic obstructive pulmonary disease and autoimmunity or prevention of a disease or condition, particularly an allergic disease or disorder, or in amelioration of the condition of a subject suffering from such a disease or disorder, including, but without being limited to, an allergic disease or disorder selected from the group consisting of asthma, rhinitis, dermatitis, drug reactions, eosinophilic diseases or disorders, esophageal and gastrointestinal allergy, or a combination thereof.

In another embodiment of the invention, the SCFA compound of formula (I) according to the present invention and as described herein in the various embodiments or a composition comprising said compound is administered alone, or, optionally, in combination with another compound in a concentration of between 0.01 mg/kg and 1000 mg/kg bodyweight, particularly between 0.1 mg/kg and 500 mg/kg body weight, particularly between 0.1 mg/kg and 100 mg/kg bodyweight, particularly between 0.1 mg/kg and 10 mg/kg bodyweight, particularly between 0.5 mg/kg and 5 mg/kg bodyweight, particularly between 1 mg/kg and 5 mg/kg bodyweight particularly in a concentration of 1 mg/kg bodyweight.

In a specific embodiment of the invention, said optional other compound administered together with the SCFA compound of formula (I) according to the present invention is a balanced salt solution as disclosed herein, particularly, said balanced salt solution is optimized for the conditions in the nasal cavities, particularly, said balanced salt solution is Locke-Ringer solution.

In another embodiment, the SCFA compound of formula (I) according to present invention or a composition as disclosed herein comprising said SCFA compound of formula (I) and optionally a balanced salt solution as disclosed herein can be administered to a subject before, on the day of, or one or more days after the viral infection, to effectively reduce the viral titer in the treated subject. In a specific embodiment, said compound or composition of the invention can be administered to a subject one day after the infection. Surprisingly, such a post-infection treatment was found to be as effective as a treatment before or at the day of infection. The compound or composition according to the present invention and as described herein may be administered in a single dose or multiple doses throughout a 24-hour time period.

In a specific embodiment, said SCFA compound of formula (I) according to the invention and as described herein is propionic acid or a pharmaceutically acceptable salt thereof.

In a specific embodiment of the invention, said viral infection is, without being limited thereto, selected from the group consisting of Influenza virus, respiratory syncytial virus, metapneumonia virus (MPV), human immunodeficiency virus, vaccinia virus, variola virus, dengue virus, coxsackie virus, hepatitis A virus, poliovirus, rhinovirus, Herpes simplex, type 1, Herpes simplex, type 2, Varicella-zoster virus, Epstein-barr virus, Human cytomegalovirus, Human herpesvirus, Hepatitis B virus, Hepatitis C virus, yellow fever virus, dengue virus, West Nile virus, Measles virus, Mumps virus, Parainfluenza virus, Human metapneumovirus, Human papillomavirus, Rabies virus, Rubella virus, Human bocavirus, and Parvovirus B19 infection.

In another specific embodiment of the invention, said viral infection is an Influenza virus infection.

In particular, the SCFA compound of formula (I) or a composition comprising the SCFA compound of formula (I) according to the invention and as described herein in the various embodiments, particularly a propionic acid or a pharmaceutically acceptable salt thereof, or a composition comprising propionic acid, or a pharmaceutically acceptable salt thereof, optionally together with a balanced salt solution as disclosed herein, can also be used for transmucosal administration, particularly for sublingual, particularly for intranasal administration to a subject for the treatment, prevention or amelioration of virally conferred protection or enhancement of allergy subsequent to infection, or the virally-induced development of immunodeficiency in chronic infection.

Other embodiments of the invention relate to a method for inducing antigen-specific T cells in a subject, particularly of antigen-specific CD4+ T cells or CD8+ T cells or both, particularly in the airways of said subject, comprising transmucosally, particularly intranasally, particularly sublingually administering to said subject in need thereof a SCFA compound of formula (I) according to the invention and as described herein in the various embodiments or a pharmaceutically acceptable salt thereof, or a composition comprising the SCFA compound of formula (I) according to the invention and as described herein in the various embodiments, or a pharmaceutically acceptable salt thereof, particularly a propionic acid or a composition comprising propionic acid, or a pharmaceutically acceptable salt thereof, optionally together with a balanced salt solution as disclosed herein, which leads to a reduction of the amount of T helper 2 (Th2) cell-derived cytokines in a subject treated with said compound or composition, particularly in the airways of said subject. Transmucosal, particularly sublingual, particularly intranasal administration of the compound or composition according to the invention may thus be used for the treatment or prevention of a disease or disorder mediated by T helper 2 (Th2) cell-derived cytokines, or for amelioration of the condition of a subject suffering from such a disease or disorder.

Other embodiments of the invention relate to a method for treatment, prevention, or attenuation of viral infections and/or virus-induced exacerbations of allergic diseases or disorders such as asthma, chronic obstructive pulmonary disease and allergy or autoimmunity comprising transmucosally, particularly sublingually, particularly intranasally administering to a subject in need of such a treatment a therapeutically effective amount of a SCFA compound of formula (I) or a composition comprising the compound of formula (I), or a pharmaceutically acceptable salt thereof, particularly in a therapeutically effective amount, optionally, together with a pharmaceutically acceptable carrier. In particular, said composition may further comprise a balanced salt solution as disclosed herein.

In a specific embodiment, said SCFA compound of formula (I) according to the invention and as described herein is propionic acid or a pharmaceutically acceptable salt thereof.

In one embodiment of the invention a method of inducing, promoting or enhancing an immune response to an immunogen in a subject is provided, for example, an immunogen comprised in a vaccine, particularly a viral vaccine comprising transmucosally administering to a subject in need thereof comprising a SCFA compound of formula (I) or a composition as described herein, or a pharmaceutically acceptable salt thereof, particularly in a therapeutically effective amount, optionally, together with a pharmaceutically acceptable carrier and/or a balanced salt solution disclosed herein, wherein the transmucosal administration is effected by intranasal, buccal, oral, transmucosal, intratracheal, intraurinary tract, intravaginal, sublingual, intrabronchial, intrapulmonary and/or transdermal administration.

In a specific embodiment of the invention a method of inducing, promoting or enhancing an immune response to an immunogen in a subject is provided, wherein transmucosal administration of said compound or composition, optionally together with a pharmaceutically acceptable carrier and/or a balanced salt solution as disclosed herein, is effected intranasally or by inhalation. In a specific embodiment of the invention a method of inducing, promoting or enhancing an immune response to an immunogen in a subject is provided, wherein transmucosal administration of said compound or composition is effected by sublingual administration.

In a specific embodiment of the invention, said viral infection is, without being limited thereto, selected from the group consisting of Influenza virus, respiratory syncytial virus, metapneumonia virus (MPV), human immunodeficiency virus, vaccinia virus, variola virus, dengue virus, coxsackie virus, hepatitis A virus, poliovirus, rhinovirus, Herpes simplex, type 1, Herpes simplex, type 2, Varicella-zoster virus, Epstein-barr virus, Human cytomegalovirus, Human herpesvirus, Hepatitis B virus, Hepatitis C virus, yellow fever virus, dengue virus, West Nile virus, Measles virus, Mumps virus, Parainfluenza virus, Human metapneumovirus, Human papillomavirus, Rabies virus, Rubella virus, Human bocavirus, and Parvovirus B19 infection.

The above compound or composition can also be used in a method for preparing a medicament.

In still another embodiment, the invention relates to a SCFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier, and/or a balanced salt solution, for use as an adjuvant in inducing, promoting or enhancing an immune response in a subject treated with an immunogen, for example, an immunogen comprised in a vaccine, particularly a viral vaccine upon transmucosal administration, particularly upon intranasal administration, particularly upon sublingual administration.

In one embodiment, the invention relates to a method of inducing, promoting or enhancing an immune response against an immunogen in a subject, comprising: (a) transmucosally, particularly sublingually, particularly intranasally administering an immunogen to a subject in need thereof in an immunogenically effective amount; and (b) transmucosally, particularly intranasally, particularly sublingually administering a SCFA compound of formula (I) according to the invention and as described herein in the various embodiments or a pharmaceutically acceptable salt thereof, or a composition comprising the SCFA compound of formula (I) according to the invention and as described herein in the various embodiments and optionally a balanced salt solution as disclosed herein.

In one embodiment, the invention relates to the use of a SCFA compound of formula (I) according to the invention and as described herein in the various embodiments or of a pharmaceutically acceptable salt thereof, or a composition comprising the SCFA compound of formula (I) according to the invention and as described herein in the various embodiments, or a pharmaceutically acceptable salt thereof, as an adjuvant for inducing, promoting or enhancing an immune response against an immunogen, wherein said SCFA compound of formula (I) is administered to a subject in need thereof by transmucosal administration, particularly by sublingual administration, particularly by intranasal administration. In particular, said immune response is primarily triggered or induced by a physiologically balanced salt solution as disclosed herein.

The above compound or composition can also be used for preparing an adjuvant formulation or a medicament.

In certain embodiments of the invention, said viral vaccines are selected from the group consisting of vaccines towards Influenza virus, respiratory syncytial virus, metapneumonia virus (MPV), human immunodeficiency virus, vaccinia virus, variola virus, dengue virus, coxsackie virus, hepatitis A virus, poliovirus, rhinovirus, Herpes simplex, type 1, Herpes simplex, type 2, Varicella-zoster virus, Epstein-barr virus, Human cytomegalovirus, Human herpesvirus, Hepatitis B virus, Hepatitis C virus, yellow fever virus, dengue virus, West Nile virus, Measles virus, Mumps virus, Parainfluenza virus, Human metapneumovirus, Human papillomavirus, Rabies virus, Rubella virus, Human bocavirus, and Parvovirus B19 infections.

Further contemplated are vaccines selected from the group consisting of a diphtheria vaccine, a pertussis vaccine, a tetanus vaccine, a polio vaccine, a hepatitis A vaccine, a hepatitis B vaccine, a rabies vaccine, a measles vaccine, a rubella vaccine, ain influenza vaccine, a mumps vaccine, a varicella vaccine, a rota vaccine, a smallpox vaccine, a yellow fever vaccine, a mite-mediated encephalitis vaccine, an Hib vaccine, a typhoid vaccine, a cholera vaccine, a BCG vaccine, a pneumococcus vaccine and a vaccine against meningitis caused by *Neeisseria meningitidis*.

Myeloid precursor cells, but particularly dendritic cells (DCs) are crucial cell types required for inducing inflammatory responses, such as asthma. These cells capture antigens/allergens in the lung and transport them to the draining lymphoid tissue where they activate T cells. These T cells then migrate back to the lung where they are reactivated by lung-resident dendritic cells, and elicit their effector function causing many of the symptoms of asthma (plus list of diseases). Myeloid precursor cells, but particularly dendritic cells thus represent an important rate-limiting step in the development of Th2 and Th17 driven inflammation and modifying their function is a powerful means of regulating inflammation.

It has now been surprisingly found within the scope of the present invention that transmucosal administration, particularly sublingual, particularly intranasal administration of short chain fatty acids (SCFA), particularly of propionic acid or a pharmaceutically acceptable salt thereof, can lead to a modulation of the number and/or the activation state of myeloid precursor cells, but particularly of dendritic cells (DCs) in an individual, particularly in the airways of an individual, which has major implications on the use and the effectiveness of said compounds in the prevention or amelioration of viral infections, autoimmune diseases, and/or allergic disorders/diseases. It has further been surprisingly found within the scope of the present invention that transmucosal administration, particularly sublingual, particularly intranasal administration, of short chain fatty acids (SCFA), particularly of propionic acid or a pharmaceutically acceptable salt thereof, is capable of reducing the release of cytokines from Th2 cells in model animals, but particularly the release of IL-4, IL8 and/or IL-17A. These compounds were further shown to reduce systemic IgE levels in model animals while leaving other important antibody isotypes, including IgG2a, IgG2c and IgA, unaffected. Further, differential cell counts revealed that treatment of model animals with short chain fatty acids also lead to a reduction of eosinophils.

Accordingly, short chain fatty acids of formula (I) according to the present invention as described herein in the various embodiments, particularly propionic acid or a pharmaceutically acceptable salt thereof, can be used for transmucosal administration, particularly sublingual, particularly intranasal administration in human therapy at an early stage for the treatment or, prevention of allergic diseases, or for amelioration of the condition of a subject suffering from such a disease or disorder, particularly of a disease or disorder mediated by T helper 2 (Th2) cell-derived cytokines, including, without being limited to, IL-4, IL-5, IL-6, IL-8, IL-10, IL-13, and IL-17A, but particularly of IL-4 and/or IL-8 and/or IL-17A and/or IgE mediated diseases or disorders including, but without being limited to, allergic disorders including autoimmune diseases selected from asthma, rhinitis, dermatitis, drug reactions, esophageal and gastrointestinal allergy.

Short chain fatty acids of formula (I) according to the present invention as described herein in the various embodiments, particularly propionic acid or a pharmaceutically acceptable salt thereof, can further be used for transmucosal administration, particularly for sublingual administration, particularly for intranasal administration, in human therapy for the treatment of eosinophilic diseases or disorders comprising nodules, eosinophilia, eosinophilic rheumatism, dermatitis and swelling (NERDS).

In another embodiment, the present invention relates to a SCFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier and/or a balanced salt solution as disclosed herein, for use in transdermal administration, particularly for use in sublingual administration, particularly for use in intranasal administration in a subject, for modulating the number and/or the activation state of myeloid precursor cells, but particularly dendritic cells (DCs) in the affected tissue or organ of the treated subject In a specific embodiment, said SCFA compound of formula (I) according to the invention and as described herein is propionic acid or a pharmaceutically acceptable salt thereof.

In another embodiment, the present invention relates to a SCFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier, and/or a balanced salt solution as disclosed herein for use in a method for the prevention of development of a Th2 induced inflammatory condition in a tissue or organ of a subject, the method comprising transmucosally, particularly sublingually, particularly intranasally administering an effective amount of a compound of formula (I) to the subject, which compound modulates the number and/or the activation state of myeloid precursor cells, but particularly dendritic cells (DCs) in the affected tissue or organ of the treated subject, particularly prior to the activation of a T cell response.

In a specific embodiment, said SCFA compound of formula (I) according to the invention and as described herein is propionic acid or a pharmaceutically acceptable salt thereof.

In another embodiment, the present invention relates to a compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier and/or a balanced salt solution as disclosed herein, for use in human or animal therapy comprising administering said compound or composition transmucosally, particularly sublingually, particularly intranasally to a subject for reducing the release of cytokines from Th2 cells and/or of systemic IgE levels, while leaving other antibody isotypes, including IgG2a and IgG2c, unaffected and/or reducing eosinophil infiltration, resulting in treatment or prevention of an associated disease or disorder, or amelioration of the condition of a subject suffering from such a disease or disorder, such as an allergic disease or disorder.

In yet another embodiment, the present invention relates to a compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier and/or a balanced salt solution as disclosed herein, for use in human or animal therapy comprising administering said compound or composition transmucosally, particularly intranasally, particularly sublingually to a subject for reducing the release of cytokines from Th2 cells and/or of systemic IgE levels, while leaving other antibody isotypes, including IgG2a and IgG2c, unaffected and/or reducing eosinophil infiltration, resulting in treatment or prevention of an associated disease or disorder, or amelioration of the condition of a subject suffering from such a disease or disorder, such as an allergic disease or disorder.

In another certain embodiment, the present invention relates to a SOFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier, for use in modulating the barrier function and integrity of epithelial cells comprising administering said compound or composition transmucosally, particularly intranasally, particularly sublingually to a subject in need thereof. In particular, said composition optionally comprises a physiologically balanced salt solution as disclosed herein, which has positive effects on the barrier function and integrity of epithelial cells. Such positive effects are for instance an increased or stabilized mucociliary function, such as an increased or stabilized cilia movement and/or increased or stabilized epithelial barrier integrity.

In a specific embodiment, said SOFA compound of formula (I) according to the invention and as described herein is propionic acid or a pharmaceutically acceptable salt thereof.

In another certain embodiment, the present invention relates to a SCFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier and/or a balanced salt solution as disclosed herein for use in modulating the activity of members of the IL-1 family and the inflammasome comprising administering said compound or composition transmucosally, particularly intranasally, particularly sublingually, to a subject in need thereof.

In a specific embodiment, said SCFA compound of formula (I) according to the invention and as described herein is propionic acid or a pharmaceutically acceptable salt thereof.

In another embodiment of the invention, the SCFA compound of formula (I) according to the invention and as described herein in the various embodiments or a pharmaceutically acceptable salt thereof, or a composition comprising the SCFA compound of formula (I) according to the invention and as described herein in the various embodiments, optionally together with a balanced salt solution as disclosed herein, may be used in a method of modulating the number and/or the activation state of myeloid precursor cells, but particularly dendritic cells (DCs) in an individual, particularly in the airways of an individual comprising administering said compound or composition transmucosally, particularly intranasally, particularly sublingually, to a subject in need thereof. Said compounds or compositions can thus be used for an early stage treatment or prevention of allergic diseases, particularly of a disease or disorder mediated by T helper 2 (Th2) cell-derived cytokines, including, without being limited to, IL-4, IL-5, IL-6, IL-8, IL-10, IL-13, and IL-17A, but particularly of IL-4 and/or IL-8 and/or IL-17A and/or IgE mediated diseases or disorders including, but without being limited to, allergic disorders including autoimmune diseases selected from asthma, rhinitis, dermatitis, drug reactions, esophageal and gastrointestinal allergy.

In particular, the compound of formula (I) or a pharmaceutically acceptable salt thereof for use in a method for the prevention of development of a Th2 induced inflammatory condition in a tissue or organ of a subject, the method comprising transmucosal administering an effective amount of a compound of formula (I) to the subject, wherein said subject suffers from IgE-mediated disease or disorder and wherein the IgG and/or IgA levels in the treated subject remain unaffected or are increased.

In a specific embodiment of the invention the compound of formula (I) or a pharmaceutically acceptable salt thereof is provided for use in a method in reducing the IL-4 release from Th2 cells in a subject suffering from an IL-4 mediated disease or disorder.

Short chain fatty acids of formula (I) according to the invention and as described herein in the various embodiments, particularly propionic acid or a pharmaceutically acceptable salt thereof, can further be used in human therapy for the treatment, particularly for the early stage treatment of eosinophilic diseases or disorders comprising nodules, eosinophilia, eosinophilic rheumatism, dermatitis and swelling (NERDS).

In one embodiment, the present invention relates to a SCFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier and/or a balanced salt solution, for use in human or animal therapy comprising administering said compound or composition transmucosally, particularly intranasally, particularly sublingually, to a subject for reducing the circulating levels of immunogen-specific IgE in a subject treated with said compound and exposed to an immunogen, and thus for use in the treatment or prevention of an IgE mediated disease or disorder, or for amelioration of the condition of a subject suffering from such a disease or disorder.

In a specific embodiment, said SCFA compound of formula (I) according to the invention and as described herein is propionic acid or a pharmaceutically acceptable salt thereof, optionally together with a balanced salt solution as disclosed herein.

In one embodiment, the present invention relates to a SCFA compound of formula (I) according to the invention and as described herein in the various embodiments or to a pharmaceutically acceptable salt thereof, or to a composition comprising the SCFA compound of formula (I) according to the invention and as described herein in the various embodiments, or a pharmaceutically acceptable salt thereof, particularly in a therapeutically effective amount, optionally, together with a pharmaceutically acceptable carrier, and/or a balanced salt solution as disclosed herein for use in human or animal therapy comprising administering said compound or composition transmucosally, particularly intranasally, particularly sublingually, to a subject for reducing the number of eosinophils in a subject treated with said compound and exposed to an immunogen, particularly in the airways of said subject, and thus for use in the treatment or prevention of an eosinophilic disease or disorder, or for amelioration of the condition of a subject suffering from such a disease or disorder.

In one embodiment, the disease or disorder is an allergic disease or disorder mediated by T helper 2 (Th2) cell-derived cytokines, including, without however being limited to, IL-4, IL-5, IL-6, IL-8, IL-10, IL-13 or IL-17A, or certain combinations thereof, particularly an IL-4 and/or IL-8, and/or IL-17A mediated disease or disorder, and/or an IgE mediated disease or disorder, particularly a disease or disorder selected from the group consisting of allergic asthma, hay fever, drug allergies, allergic bronchopulmonary aspergillosis (ABPA), esophageal and a gastrointestinal allergy, *pemphigus vulgaris*, atopic dermatitis, onchocercal dermatitis, viral infections such as Respiratory Syncytial Virus infection or a combination thereof.

In one embodiment, the asthma is steroid resistant asthma, neutrophilic asthma or non-allergic asthma.

In one embodiment, the allergic disease or disorder is an eosinophilic disease or disorder, particularly a disease or disorder selected from the group consisting of nodules, eosinophilia, eosinophilic rheumatism, dermatitis and swelling (NERDS).

In another embodiment, the allergic disease or disorder is an IgE-mediated disease or disorder, particularly a disease or disorder selected from the group consisting of urticaria, eczema conjunctivitis, rhinorrhea, rhinitis, particularly allergic rhinitis, gastroenteritis, or a combination thereof.

In still another embodiment, an IgE-mediated disease or disorder comprises myeloma, multiple myeloma, Hodgkin's disease, Hyper-IgE syndrome, Wiskott-Aldrich syndrome, Chronic Obstructive Pulmonary Disease and exacerbations of Chronic Obstructive Pulmonary Disease or a combination thereof.

In certain embodiments, the invention relates to a method for modulating the number and/or the activation state of myeloid precursor cells, but particularly dendritic cells (DCs) in the affected tissue or organ, said method comprising administering transmucosally, particularly intranasally, particularly sublingually, at an early stage to a subject in need of such a treatment a therapeutically effective amount of a SCFA compound of formula (I) or of a composition comprising the compound of formula (I), or a pharmaceutically acceptable salt thereof, particularly in a therapeutically effective amount, optionally, together with a pharmaceutically acceptable carrier and/or a balanced salt solution as disclosed herein, particularly prior to the activation of a T cell response.

In particular, the invention relates to a method for the prevention of development of a Th2 induced inflammatory condition in a tissue or organ of a subject, the method comprising administering an effective amount of a compound of formula (I) to the subject transmucosally, particularly intranasally, particularly sublingually, which compound modulates the number and/or the activation state of myeloid precursor cells, but particularly dendritic cells (DCs) in the affected tissue or organ. In particular, said method comprises administering transmucosally, particularly intranasally, particularly sublingually, at an early stage to a subject in need of such a treatment a therapeutically effective amount of a SCFA compound of formula (I) or of a composition comprising the compound of formula (I), or a pharmaceutically acceptable salt thereof, particularly in a therapeutically effective amount, optionally, together with a pharmaceutically acceptable carrier and/or a balanced salt solution as disclosed herein, particularly prior to the activation of a T cell response.

Other embodiments of the invention relate to a method for the treatment or prevention of a disease or disorder mediated by T helper 2 (Th2) cell-derived cytokines, including, without however being limited to, IL-4, IL-5, IL-6, IL-8, IL-10, IL-13 or IL-17A, or certain combinations thereof, particularly an IL-4 and/or IL-8, and/or IL-17A mediated disease or disorder, and/or an IgE mediated disease or disorder and/or an eosinophilic disease or disorder, or for amelioration of the condition of a subject suffering from such a disease or disorder, said method comprising administering transmucosally, particularly intranasally, particularly sublingually, to a subject in need of such a treatment a therapeutically effective amount of a SCFA compound of formula (I) or of a composition comprising the compound of formula (I), or a pharmaceutically acceptable salt thereof, particularly in a therapeutically effective amount, optionally, together with a pharmaceutically acceptable carrier and/or a balanced salt solution.

In one embodiment, the invention relates to a method for selectively controlling, particularly for selectively reducing, allergen-specific IgE antibody levels in a subject suffering from IgE-mediated disease or disorder comprising administering transmucosally, particularly intranasally, particularly sublingually, to a subject in need of such a treatment a therapeutically effective amount of a SCFA compound of formula (I) or of a composition comprising the compound of formula (I), or a pharmaceutically acceptable salt thereof, in a therapeutically effective amount, optionally, together with a pharmaceutically acceptable carrier and/or a balanced salt solution. In a specific embodiment, such a treatment does not affect or increases IgG levels, particularly IgG2a, IgG2c levels, and/or IgA levels, in the treated subject.

In one embodiment, the invention relates to a method for reducing the release of IL-4, and/or IL-8, and/or IL-17A, from Th2 cells in a subject suffering from an IL-4, and/or IL-8, and/or IL-17A mediated disease or disorder comprising administering transmucosally, particularly intranasally, particularly sublingually, to a subject in need of such a treatment a therapeutically effective amount of a SCFA compound of formula (I) or of a composition comprising the compound of formula (I), or a pharmaceutically acceptable salt thereof, particularly in a therapeutically effective amount, optionally, together with a pharmaceutically acceptable carrier and/or a balanced salt solution. In a specific embodiment, such a treatment also reduces the allergen-specific IgE antibody levels in a subject, but does not affect or increases IgG levels, particularly IgG2a, IgG2c levels, and/or IgA levels, in the treated subject.

In another embodiment, the invention relates to a method for use in the treatment or prevention of an allergic disease or disorder, or for amelioration of the condition of a subject suffering from an allergic disease or disorder, including, but without being limited to, an allergic disease or disorder selected from the group consisting of asthma, rhinitis, dermatitis, drug reactions, eosinophilic diseases or disorders, esophageal and gastrointestinal allergy, or a combination thereof comprising administering transmucosally, particularly intranasally, particularly sublingually, to a subject in need of such a treatment a therapeutically effective amount of a SCFA compound of formula (I) or of a composition comprising the compound of formula (I), or a pharmaceutically acceptable salt thereof, particularly in a therapeutically effective amount, optionally, together with a pharmaceutically acceptable carrier and/or a balanced salt solution.

In a specific embodiment, said SCFA compound of formula (I) according to the invention and as described herein is propionic acid or a pharmaceutically acceptable salt thereof.

In one embodiment, the allergic disease or disorder is an IL-4- and/or IL-8- and/or IL-17A-mediated disease or disorder and/or an IgE mediated disease or disorder, particularly a disease or disorder selected from the group consisting of allergic asthma, hay fever, drug allergies, allergic bronchopulmonary aspergillosis (ABPA), esophageal and a gastrointestinal allergy, *pemphigus vulgaris*, atopic dermatitis, onchocercal dermatitis, or a combination thereof.

In one embodiment, the allergic disease or disorder is an eosinophilic disease or disorder, particularly a disease or disorder selected from the group consisting of nodules, eosinophilia, eosinophilic rheumatism, dermatitis and swelling (NERDS).

In another embodiment, the allergic disease or disorder is an IgE-mediated disease or disorder, particularly a disease or disorder selected from the group consisting of urticaria, eczema conjunctivitis, rhinorrhea, rhinitis, particularly allergic rhinitis, gastroenteritis, or a combination thereof.

In still another embodiment, an IgE-mediated disease or disorder comprises myeloma, multiple myeloma, Hodgkin's disease, Hyper-IgE syndrome, Wiskott-Aldrich syndrome, or a combination thereof.

In certain embodiments, the present invention provides a method for the manufacture of the compositions according to the invention and as described herein in the various embodiments comprising one or more SOFA compound of formula (I) according to the invention and as described herein in the various embodiments as active ingredients which process comprises mixing one or more SCFA compounds of formula (I) with an inert carrier or excipient that is acceptable to the target organism that is in need of the treatment, optionally together with a balanced salt solution.

In several embodiments of the inventions, the balanced salt solution as used therein is Locke-Ringer solution.

In various embodiments of the invention, administration of SOFA as disclosed herein or a composition comprising said SOFA as disclosed herein, particularly propionic acid or a pharmaceutically acceptable salt thereof, or a composition comprising propionic acid or a pharmaceutically acceptable salt thereof, together with a balanced salt solution as disclosed herein, particularly Locke-Ringer solution leads to an elevated Th1 immune response and/or reduced Th2 immune response compared to the single administration of said SOFA or composition comprising said SCFA or balanced salt solution.

In various embodiments of the inventions, administration of SCFA as disclosed herein or a composition comprising said SCFA as disclosed herein, particularly propionic acid or a pharmaceutically acceptable salt thereof, or a composition comprising propionic acid or a pharmaceutically acceptable salt thereof, together with a balanced salt solution as disclosed herein, particularly Locke-Ringer solution leads to a more efficient treatment of asthma, chronic obstructive pulmonary disease and autoimmunity compared to the single administration of said SCFA or composition comprising said SCFA or balanced salt solution. In particular, wherein said diseases or disorders are caused by viral infections.

Definitions

The technical terms and expressions used within the scope of this application are generally to be given the meaning commonly applied to them in the pertinent art if not otherwise indicated herein below.

As used in this specification and the appended claims, the singular forms "a", "an", and "the" include plural referents unless the context clearly dictates otherwise. Thus, for example, reference to "a compound" includes one or more compounds.

"Alkyl" as such means a straight-chained or branched saturated aliphatic hydrocarbon having from 1 to 10 carbon atoms, wherein the alkyl group may be unsubstituted or substituted with one or more, same or different, substituents selected from the group consisting of hydroxyl, amino, carboxylic acid, halogen, cyano, or nitro. Preferred are $C_1$-$C_6$ alkyl, such as methyl, ethyl, n-propyl, isopropyl, n-butyl, isobutyl, tert-butyl, n-pentyl (amyl), 2-pentyl (sec-pentyl), 3-pentyl, 2-methylbutyl, 3-methylbutyl (=iso-pentyl or iso-amyl), 3-methylbut-2-yl, 2-methylbut-2-yl, 2,2-dimethylpropyl (=neopentyl), n-hexyl, iso-hexyl, sec.-hexyl, tert.-hexyl and the like. Most preferred are $C_1$-$C_4$ alkyl, such as methyl, ethyl, n-propyl, isopropyl, n-butyl, isobutyl, tert-butyl.

"Hydroxyalkyl" stands for one of the above-defined alkyl groups wherein at least one hydrogen atom is replaced by a hydroxyl group and wherein the hydroxyalkyl group may be unsubstituted or substituted with one or more, same or different, substituents selected from the group consisting of hydroxyl, amino, carboxylic acid, halogen, cyano, or nitro. Typical representatives are —$CH_2OH$, —$CH_2CH_2OH$, —$CH(OH)$—$CH_3$, —$CH(OH)CH_2CH_3$, $CH_2CH(CH_2CH_2OH)CH_2CH$ etc.

"Aryl" means a monovalent, monocyclic, bicyclic or tricyclic, aromatic carbocyclic hydrocarbon radical, preferably a 6-14 member aromatic ring system. Preferred aryl groups include, but are not limited to phenyl, naphthyl, phenanthrenyl, and anthracenyl, wherein the aryl group may be unsubstituted or substituted with one or more, same or different substituents selected from the group consisting of halogen; alkyl; alkyloxy; cyano, trifluoro, nitro, amino, hydroxyl.

"Alkoxy" means —O-alkyl, wherein alkyl has the meaning given above. "Halogen" means fluorine, chlorine, bromine, or iodine, preferably fluorine, chlorine or iodine.

"Polyalkylene glycol" means a moiety that comprises at least two aklylene glycol units such as —O-alkyl-O-alkyl-O- moiety wherein alkyl have the meaning given above. The polyalkylene glycol moiety may be solely comprised of polyalkylene glycol, or may be part of a larger structure, such as polyoxyalkylated glycerol and other polyoxyalkylated polyols such as polyoxyethylated sorbitol or polyoxyethylated glucose. The number of alkylene units may vary and is greater than 1. Preferred, polyalkylene glycol are polyethylene glycol (PEG) or polypropylene glycol (PPG). Most preferred polyalkylene glycol are PEG wherein the number of ethylene units may vary from 8 to 150.000 or more, particularly from 10 to 80.000, more particularly from 20 to 10.000.

The term "compound of formula (I)" and "composition comprising the compound of formula (I)" is meant to also refer to a pharmaceutically acceptable salt of the compound of formula (I).

The term "propionate" refers to the pharmaceutically acceptable salt of propionic acid such as, for example, the sodium salt of propionic acid.

The term "pharmaceutically acceptable salts" include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease related to an undesired immune response from occurring in a subject which may be predisposed to the disease; (b) inhibiting the disease, i.e. arresting its development; or (c) relieving the disease, i.e. causing regression of the disease.

A "patient" or "subject" for the purposes of the present invention is used interchangeably and meant to include both humans and other animals, particularly mammals, and other organisms. Thus, the methods are applicable to both human therapy and veterinary applications. In the preferred embodiment the patient or subject is a mammal, and in the most preferred embodiment the patient or subject is a human.

The term "attenuation" as used herein refers to reduction of a viral infection in a subject or in a tissue of a subject, particularly in lung tissue of a subject, i.e. reduction or clearance of the amount of virus or viral load. The particular degree or level of the reduction or clearance is at least 15%, 25%, 35%, 50%, 65%, 75%, 80%, 85%, 90%, 95%, 98% or more.

The term "adjuvant" as used herein refers to a substance that increases or promotes the ability of an immunogen (i.e., antigen) to stimulate an immune response against the immunogen in the subject subjected to the immunogen. In particular embodiments, the adjuvant increases the immune response against the immunogen by at least 2, 3, 4, 5, 10, 15, 20, 30, 40, 50, 60, 75, 100, 150, 500, 1000-fold or more. In other embodiments, the adjuvant reduces the amount of immunogen required to achieve a particular level of immune response (cellular and/or humoral and/or mucosal), e.g., a reduction of at least 15%, 25%, 35%, 50%, 65%, 75%, 80%, 85%, 90%, 95%, 98% or more. An adjuvant can further be a substance that prolongs the time over which an immune response, optionally protective immune response, is sustained (e.g., by at least a 2-fold, 3-fold, 5-fold, 10-fold, 20-fold longer time period or more).

The terms "myeloid precursors", "myeloid lineage" or "myeloid cells" refer all to multipotent stem cells as one of two lineages of hematopoietic cells, which are able to develop into monocytes, macrophages, dendritic cells, neutrophils, eosinophils, basophils, megacaryocytes, platelets or erythrocytes.

A "modulating compound" refers to a compound as described herein in the various embodiments, which may either up-regulate (e.g., activate or stimulate), down-regulate (e.g., inhibit or suppress) or otherwise change a functional property or biological activity of a target molecule or gene. A modulating compound may act to modulate a target molecule or a gene encoding said target molecule either directly or indirectly. In certain embodiments, a modulating compound may be an activating compound or an-inhibiting compound.

The "modulation of a Th2 or Th2-like immune response towards a Th1 immune response" refers to a change from a "humoral immune response" executed mainly by antibodies, B cells, plasma cells and/or memory B cells towards a "cellular immune response, executed mainly by CD8+ T cells and phagocytes, e.g. macrophages. This modulation implements also a change in the cytokine composition which is characteristic for each of the two distinct T helper cell mechanisms. A Th2 or Th2-like immune response is mediated by IL-4, IL-5, IL-6, IL-8, IL-10, IL-13, and/or IL-17A, particularly IL-4 and/or IL-8 and/or IL-17A, whereas a Th1 immune response is mediated by interferon-gamma (IFN-gamma), IL-2, and tumor necrosis factor-alpha (TNF-alpha). Further "modulation" means particularly prior to the activation of a T cell response.

The expressions "pharmaceutical composition" and "therapeutical composition" are used herein interchangeably in the widest sense. They are meant to refer, for the purposes of the present invention, to a therapeutically effective amount of the active ingredient, i.e. the SCFA compound of formula (I) or a pharmaceutically acceptable salt thereof, optionally, together with a pharmaceutically acceptable carrier and/or a balanced salt solution.

It embraces compositions that are suitable for the curative treatment, the control, the amelioration, an improvement of the condition or the prevention of a disease or disorder in a human being or a non-human animal. Thus, it embraces pharmaceutical compositions for the use in the area of human or veterinary medicine. Such a "therapeutic composition" is characterized in that it embraces at least one SCFA compound of formula (I) compound or a physiologically acceptable salt thereof, and optionally a carrier and/or a balanced salt solution whereby the salt and the carrier and balanced salt solution are tolerated by the target organism that is treated therewith.

The terms "balanced salt solution" or "physiologically balanced salt solution" as used herein refers to a salt solution with stable osmolality and pH value between 6.5 and 7.6 and defined ion composition reflecting the ratio of ions in the human body, particularly the nasal respiratory mucosa. An example for a suitable balanced salt solution according to the present invention is Locke-Ringer solution (osmolality of about 328 mosmol; pH of about 7.4). However, also other salt solution may be suitable, if the ion composition of these salt solutions reflects essentially the ratio of ions in the human body and contains a biological inert buffer substance.

A "therapeutically effective amount" refers to that amount which provides a therapeutic effect for a given condition and administration regimen. In particular, "therapeutically effective amount" means an amount that is effective to prevent, alleviate or ameliorate symptoms of the disease or prolong the survival of the subject being treated, which may be a human or non-human animal. Determination of a therapeutically effective amount is within the skill of the person skilled in the art.

The therapeutically effective amount or dosage of a compound according to this invention can vary within wide limits and may be determined in a manner known in the relevant art. The dosage can vary within wide limits and will, of course, have to be adjusted to the individual requirements in each particular case.

The term "transmucosal" administration refers to various administration routes whereas the compound is absorbed by the mucosa of any part of the body. Transmucosal administration comprises, but is not limited to, i.e. intranasal, buccal, oral transmucosal, intratracheal, intraurinary tract, intravaginal, sublingual, intrabronchial, intrapulmonary and transdermal administration.

An "immunogenically effective amount" refers to that amount of an immunogen which provides an active immune response (cellular and/or humoral) in a subject. In some embodiments of the invention, said immune response is sufficient to provide a protective effect, which does not need to be complete or permanent. Determination of an immunogenically effective amount is within the skill of the person skilled in the art.

An "adjuvant effective amount" refers to that amount of an adjuvant that enhances or stimulates the active immune response (cellular and/or humoral or optionally an active mucosal immune response) provided by the immunogen in a subject when subjected to the immunogen.

In the context of protective immune responses, the term "adjuvant effective amount" refers to an amount of the adjuvant that is needed to accelerate the induction of the immune response in the host and/or may be sufficient to reduce the need for booster immunizations to achieve protection.

In the context of prolongation of an immune response, the term "adjuvant effective amount" refers to an amount that prolongs the time period over which an immune response, optionally protective immune response, is sustained.

Determination of an adjuvant effective amount in the above addressed contexts is within the skill of the person skilled in the art.

The SCFAs of formula (I) may be provided as such or in form of a composition, particularly a pharmaceutical composition. Said compositions may comprise additional medicinal agents, balanced salt solutions, pharmaceutical agents, carriers, buffers, adjuvants, dispersing agents, diluents, and the like depending on the intended use and application. In particular, said composition comprises a balanced salt solution, such as Locke-Ringer solution. Saline solutions exhibit specific influences on the functionality of the mucociliary system, especially on the frequency of ciliary movement, depending on the composition, the osmolality and the pH-value of the solution. Balanced salt solutions containing potassium and calcium ions and a buffer (like Locke-Ringer solution) exhibited an elevation or stabilization of the frequency of ciliary movement of the bronchial epithelium as pure isotonic sodium chloride.

Administration of the suitable (pharmaceutical) compositions containing the active ingredient according to the invention and as disclosed herein, may be effected by routes of administration, e.g., by intranasal, buccal, oral, transmucosal, intratracheal, intraurinary tract, intravaginal, sublingual, intrabronchial, intrapulmonary and transdermal administration.

The composition as described herein is a liquid, liquid spray, microspheres, semisolid, gel, or powder for transmucosal administration, e.g. intranasal, buccal, oral transmucosal, intratracheal, intraurinary tract, intravaginal, sublingual, intrabronchial, intrapulmonary and/or transdermal administration. Further, the composition is a solid dosage form for buccal, oral transmucosal and/or sublingual administration. Intranasal, buccal, oral intratracheal, intraurinary tract, intravaginal, transmucosal and sublingual administrations lead to the disintegration of the composition as described herein in an oral cavity at body temperature and optionally may adhere to the body tissue of the oral cavity. Additionally, the composition as disclosed herein further may include one or more excipient, diluent, binder, lubricant, glidant, disintegrant, desensitizing agent, emulsifier, mucosal adhesive, solubilizer, suspension agent, viscosity modifier, ionic tonicity agent, buffer, carrier, balanced salt solution, surfactant, flavor, or mixture thereof.

In a specific aspect the composition is formulated as a tablet, pill, bioadhesive patch, sponge, film, lozenge, hard candy, wafer, sphere, lollipop, disc-shaped structure, or spray.

Transmucosal administration is generally rapid because of the rich vascular supply to the mucosa and the lack of a stratum corneum in the epidermis. Such drug transport typically provides a rapid rise in blood concentrations, and similarly avoids the enterohepatic circulation and immediate destruction by gastric acid or partial first- pass effects of gut wall and hepatic metabolism. Drugs typically need to have prolonged exposure to a mucosal surface for significant drug absorption to occur.

The transmucosal routes can also be more effective than the oral route in that these routes can provide for relatively faster absorption and onset of therapeutic action. Further, the transmucosal routes can be preferred for use in treating patients who have difficulty in swallowing tablets, capsules, or other oral solids, or those who have disease-compromised intestinal absorption. Accordingly, there are many advantages to transmucosal administration of SCFAs.

In either of the intranasal or buccal routes, drug absorption can be delayed or prolonged, or uptake may be almost as rapid as if an intravenous bolus were administered. Because of the high permeability of the rich blood supply, the sublingual route can provide a rapid onset of action.

The intranasal compositions of the invention, but particularly an intranasal composition comprising propionic acid or a pharmaceutically acceptable salt thereof, can be administered by any appropriate method according to their form. A composition including microspheres or a powder can be administered using a nasal insufflator device. Examples of these devices are well known to those of skill in the art, and include commercial powder systems such as Fisons Lomudal System. An insufflator produces a finely divided cloud of the dry powder or microspheres. The insufflator is preferably provided with a mechanism to ensure administration of a substantially fixed amount of the composition. The powder or microspheres can be used directly with an insufflator, which is provided with a bottle or container for the powder or microspheres. Alternatively, the powder or microspheres can be filled into a capsule such as a gelatin capsule, or other single dose device adapted for nasal administration. The insufflator preferably has a mechanism to break open the capsule or other device. Further, the composition can provide an initial rapid release of the active ingredient followed by a sustained release of the active ingredient, for example, by providing more than one type of microsphere or powder. Further, alternative methods suitable for administering a composition to the nasal cavity will be well known by the person of ordinary skill in the art. Any suitable method may be used. For a more detailed description of suitable methods reference is made to EP2112923, EP1635783, EP1648406, EP2112923 (the entire contents of which are incorporated herein by reference).

The compounds of the present invention and the pharmaceutical compositions containing said compounds may be further administered intranasally, i.e. by inhalation and thus may be formulated in a form suitable for intranasal administration, i.e. as an aerosol or a liquid preparation.

One exemplary formulation for intranasal delivery of the compound according to the invention and as described herein, but particularly of propionic acid or a pharmaceutically acceptable salt thereof, is a liquid preparation, preferably an aqueous based preparation, suitable for application as drops into the nasal cavity.

Alternatively, a liquid preparation may be placed into an appropriate device so that it may be aerosolized for inhalation through the nasal cavity. For example, the therapeutic agent may be placed into a plastic bottle atomizer. In one embodiment, the atomizer is advantageously configured to allow a substantial amount of the spray to be directed to the upper one-third region or portion of the nasal cavity. For example, as delivery device the 3K®-System from the company Ursatec Verpackung GmbH (Germany) may be used. The 3K®-System is a patented, microbiologically safeguarded dosing system which is especially suitable for administration of liquid pharmaceuticals via the nasal route. With conventional multidose-systems, the outlet openings of the dosing units are not protected. Impurities and germs can contaminate the container and the solution. Therefore, the contents of such containers must be adequately protected against microbiological deterioration by the addition of suitable preservatives. However, preservatives are harmful and have especially negative effects on the physiological mucociliary defence system of the nasal mucosa.

Additionally, the liquid preparation may be aerosolized and applied via an inhaler, such as a metered-dose inhaler. One example of a preferred device is that disclosed in U.S. Pat. No. 6,715,485, and which involves a bi-directional delivery concept. In using the device, the end of the device having a sealing nozzle is inserted into one nostril and the patient or subject blows into the mouthpiece. During exhalation, the soft palate closes due to positive pressure thereby separating the nasal and oral cavities. The combination of closed soft palate and sealed nozzle creates an airflow in which drug particles are released entering one nostril, turning 180 degrees through the communication pathway and exiting through the other nostril, thus achieving bi-directional flow.

The compound according to the invention and as described herein, but particularly propionic acid or a pharmaceutically acceptable salt thereof, may also be delivered in the form of a dry powder, as in known in the art. An example of a suitable device is the dry powder nasal delivery device marketed under the name DIRECTHALER™ nasal, and which is disclosed in PCT publication No. 96/222802. This device also enables closing of the passage between the nasal and oral cavity during dose delivery. Another device for delivery of a dry or liquid preparation is the device sold under the trade designation OPTINOSE™.

Further examples of suitable delivery devices are provided in WO2002068029, EP2462972, the disclosure, of which is incorporated herein by reference.

In the methods of the invention the animal can be a rodent, primate, human or other animal with a nasal cavity. Examples of suitable pharmaceutical carriers, excipients and/or diluents are well known in the art and include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well known conventional methods. Suitable carriers may comprise any material which, when combined with the biologically active compound of the invention, retains the biological activity.

Efforts have been made in the art to chemically modify the barrier properties of skin to permit the penetration of certain agents, enhance the effectiveness of the agent being delivered, enhance delivery times, reduce the dosages delivered, reduce the side effects from various delivery methods, reduce patient reactions, and so forth.

In this regard, penetration enhancers have been used to increase the permeability of the dermal surface to drugs, and are often proton accepting solvents such as dimethyl sulfoxide (DMSO) and dimethylacetamide. Other penetration enhancers that have been studied and reported as effective include 2-pyrrolidine, N,N-diethyl-m-toluamide (Deet), 1-dodecal-azacycloheptane-2-one N,N-dimethylformamide, N-methyl-2-pyrrolidine, calcium thioglycolate, hexanol, fatty acids and esters, pyrrolidone derivatives, derivatives of 1,3-dioxanes and 1,3-dioxolanes, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one-2-dodecylacetic acid, and aminoalcohol derivatives, including derivatives of 1,3-dioxanes, among others.

Preparations for transmucosal administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Transmucosal vehicles may include sodium chloride solution, Ringer's dextrose, dextrose and sodium chloride, lactated Ringer's, or fixed oils. Preservatives and other additives may also be present including, for example, antimicrobials, anti-oxidants, chelating agents, and inert gases and the like. In addition, the pharmaceutical composition of the present invention might comprise proteinaceous carriers, like, e.g., serum albumin or immunoglobulin, preferably of human origin.

The compounds of the present invention and as described herein in the various embodiments and the pharmaceutical compositions containing said compounds may be administered topically to body surfaces and thus be formulated in a form suitable for topical administration. Suitable topical formulations include gels, ointments, creams, lotions, drops and the like. For topical administration, the compound of formula (I) is prepared and applied as a solution, suspension, or emulsion in a physiologically acceptable diluent with or without a pharmaceutical carrier.

The pharmaceutical compositions provided herein may also be administered as controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

Further examples for suitable formulations are provided in WO 2006/085983, the entire contents of which are incorporated by reference herein. For example, the SCFAs of the present invention may be provided as liposomal formulations. The technology for forming liposomal suspensions is well known in the art. When the adjuvant is an aqueous-soluble salt, using conventional liposome technology, the same can be incorporated into lipid vesicles. The lipid layer employed can be of any conventional composition and can either contain cholesterol or can be cholesterol-free. The liposomes can be reduced in size, as through the use of standard sonication and homogenization techniques. Liposomal formulations containing the adjuvant can be lyophilized, alone or with immunogen, to produce a lyophilizate which can be reconstituted with a pharmaceutically acceptable carrier, such as water, to regenerate a liposomal suspension. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The SCFA compounds of formula (I) and as described herein in the various embodiments may used in human and veterinary medicine for treating humans and animals, including avians, non-human primates, dogs, cats, pigs, goats, sheep, cattle, horses, mice, rats and rabbits.

Suitable dosages of the SCFAs according to the invention and as described herein in the various embodiments will vary depending upon the condition, administration route, age and species of the subject, and can be readily determined by those skilled in the art. The total daily dosages of the compound of formula (I) employed in both veterinary and human medicine will suitably be in the range of between 0.01 mg/kg and 1000 mg/kg body-weight, particularly between 0.1 mg/kg and 500 mg/kg body weight, particularly between 0.1 mg/kg and 100 mg/kg body-weight, particularly between 0.1 mg/kg and 10 mg/kg body-weight, particularly between 0.5 mg/kg and 5 mg/kg body-weight, particularly between 1 mg/kg and 5 mg/kg body-weight particularly in a concentration of 1 mg/kg body-weight and these may be administered as single or divided doses, and in addition, the upper limit can also be exceeded when this is found to be indicated. Such dosage will be adjusted to the individual requirements in each particular case including the specific compound(s) being administered, the route of administration, the condition being treated, as well as the patient being treated. However, the compounds can also be administered as depot preparations (implants, slow-release formulations, etc.) weekly, monthly or at even longer intervals. In such cases the dosage will be much higher than the daily one and has to be adapted to the administration form, the body weight and the concrete indication. The appropriate dosage can be determined by conducting conventional model tests, preferably animal models. An effective dose of active ingredient(s) depends at least on the nature of the condition being treated, toxicity, whether the compound(s) is being used prophylactic ally (lower doses) or against an active infection or condition, the method of delivery, and the pharmaceutical formulation, and will be determined by the clinician using conventional dose escalation studies.

If used as an adjuvant, the SCFA compound of the invention and as described herein in the various embodiments and/or the immunogen may be given in form of a single or multiple (i.e., booster) dosage.

The immunogen and adjuvant can be co-administered concurrently (e.g., within hours of each other) in the same or different composition and, in the latter case, by the same or different route. Alternatively, the adjuvant can be administered prior to or after administration of the immunogen (e.g., about 6, 12, 24, 36, 48, 72, 96 or 120 hours or more before or after administration of the immunogen).

Further, if used as an adjuvant, the SCFA compound of the invention and as described herein in the various embodiments may administered mixed with immunogen, such as viral antigens, to enhance the immune response elicited against these antigens or alternatively the compound may be chemically coupled to the immunogen directly or in the case of particles (e.g. nanoparticles or virus-like particles (VLP)) the compound could be bound to the surface or encapsulated within said particles.

Furthermore, it is envisaged that the pharmaceutical composition of the invention might comprise further biologically active agents, depending on the intended use of the pharmaceutical composition. These further biologically active agents may be e.g. physiologically balanced salt solutions, antibodies, antibody fragments, hormones, growth factors, enzymes, binding molecules, cytokines, chemokines, nucleic acid molecules and drugs. In a preferred embodiment, the pharmaceutical composition of the present invention is to be co-administered with other known immunosuppressive drug or treatments. Such immunosuppressive drugs may be selected from the group consisting of glucocorticoids, cytostatics such as methotrexate, myophenolate or azathioprine, antibodies such as T cell receptor directed antibodies or IL-4 receptor directed antibodies and drugs acting on immunophilins such as cyclosporine, tacrolimus, sirolimus and the like.

The present invention further contemplates the use of a SCFA compound of formula (I) according to the invention and as described herein in the various embodiments or a pharmaceutically acceptable salt thereof, or of a composition comprising the SCFA compound of formula (I) according to the invention and as described herein in the various embodiments, or a pharmaceutically acceptable salt thereof, in a therapeutically effective amount, optionally, together with a pharmaceutically acceptable carrier, and/or a balanced salt solution as disclosed herein, for use as an adjuvant in promoting or enhancing an immune response in a subject in need thereof.

The immunogen can be any immunogen known in the art and can be administered in any suitable form as described, for example, in WO 2006/085983, the entire contents of which are incorporated by reference herein.

For example, the immunogen can be in the form of a live, attenuated live, or killed (i.e., inactivated) organism (e.g., a bacterium or protozoan) or virus, or an extract or toxoid thereof. In other embodiments, the immunogen can be provided as an isolated component (e.g., a polypeptide or a peptide [e.g., from about 6 to 20 or 8 to 12 amino acids in length]). Further, the immunogen can be administered per se or can be expressed from a nucleic acid that is administered to the host and the immunogen expressed therefrom. The immunogen can comprise B cell and/or T cell epitopes as are known in the art. The immunogen can further be soluble or particulate (e.g., microspheres).

In the alternative, the immunogen can be present in the organism. For example, in the case of a chronic or latent infection in the subject, the subject fails to mount a sufficient immune response against the antigen. The adjuvants of the invention can be administered to the subject to induce an immune response against the antigen already present in the subject as a result of the infection.

The immunogen can be an immunogen from an infectious agent, a cancer immunogen, an allergic reaction immunogen (i.e., an allergen), a transplantation immunogen, an autoantigen, and the like as are known in the art such as those described in WO 2006/085983.

The cancer that may be treated or immunized against (i.e., prophylactic treatment) by administration to a subject of the adjuvant of the invention can be a cancer selected from the group consisting of B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, adenocarcinoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and any other cancer now known or later identified (see, e.g., Rosenberg (1996) Ann. Rev. Med. 47:481-491, the entire contents of which are incorporated by reference herein).

Further immunogens contemplated within the scope of the present invention are infectious agent immunogens that can include any immunogen suitable for protecting a subject against an infectious disease, including but not limited to microbial, bacterial, protozoal, parasitic and viral diseases.

Examples of such infectious agent immunogens are disclosed in WO 2006/085983 and can include, but are not limited to, immunogens from Hepadnaviridae including hepatitis A, B, C, D, E, F, G, etc.; Flaviviridae including human hepatitis C virus (HCV), yellow fever virus and dengue viruses; Retroviridae including human immunodeficiency viruses (HIV), simian immunodeficiency virus (SIV), and human T lymphotrophic viruses (HTLV1 and HTLV2); Herpesviridae including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B19; Arenaviridae including Lassa virus; Orthomyxoviridae including influenza viruses; Poxviridae including Orf virus, molluscum contageosum virus, smallpox virus and Monkey pox virus; Togaviridae including Venezuelan equine encephalitis virus; Coronaviridae including corona viruses such as the severe acute respiratory syndrome (SARS) virus; and Picornaviridae including polioviruses; rhinoviruses; orbiviruses; picodnaviruses; encephalomyocarditis virus (EMV); Parainfluenza viruses, adenoviruses, Coxsackieviruses, Echoviruses, Rubeola virus, Rubella virus, human papillomaviruses, Canine distemper virus, Canine contagious hepatitis virus, Feline calicivirus, Feline rhinotracheitis virus. TGE virus (swine), Foot and mouth disease virus, simian virus 5, human parainfluenza virus type 2, human metapneuomovirus, enteroviruses, and any other pathogenic virus now known or later identified (see, e.g., Fundamental Virology, Fields et al., Eds., 3<rd>ed., Lippincott-Raven, N.Y., 1996, the entire contents of which are incorporated by reference herein for the teachings of pathogenic viruses).

Further, the immunogen may be an orthomyxovirus immunogen (e.g., an influenza virus immunogen, such as the influenza virus hemagglutinin (HA) surface protein, influenza neuraminidase protein, the influenza virus nucleoprotein (NP) antigen or inactivated influenza virions, or an equine influenza virus immunogen), or a metapneumonia virus immunogen, or a lentivirus immunogen (e.g., an equine infectious anemia virus immunogen, a SIV immunogen, or a HIV immunogen, such as, e.g., HIV or SIV gp120, gp160, gp41, or matthdcapsid protein, or the gag, pol or env gene products). The immunogen may also be an arenavirus immunogen (e.g., Lassa fever virus immunogen, such as the Lassa fever virus nucleocapsid protein gene and the Lassa fever envelope glycoprotein gene), a Picornavirus immunogen (e.g., a Foot and Mouth Disease virus immunogen), a poxvirus immunogen (e.g., a vaccinia immunogen, such as the vaccinia L1 or L8 genes), an Orbivirus immunogen (e.g., an African horse sickness virus immunogen), a flavivirus immunogen (e.g., a yellow fever virus immunogen, a West Nile virus immunogen, or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS immunogens), a norovirus immunogen (e.g., a Norwalk virus immunogen), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio antigen, herpes antigen (e.g., CMV, EBV, HSV antigens) mumps antigen, measles antigen, rubella antigen, diptheria toxin or other diptheria antigen, pertussis antigen, hepatitis (e.g., hepatitis A or hepatitis B) antigen (e.g., HBsAg, HBcAg, HBeAg), or any other vaccine immunogen known in the art.

In particular, the immunogen may be from an influenza virus, respiratory syncytial virus, metapneumonia virus (MPV), human immunodeficiency virus, vaccinia virus, variola virus, dengue virus, coxsackie virus, hepatitis A virus, poliovirus, rhinovirus, Herpes simplex, type 1, Herpes simplex, type 2, Varicella-zoster virus, Epstein-barr virus, Human cytomegalovirus, Human herpesvirus, Hepatitis B virus, Hepatitis C virus, yellow fever virus, dengue virus, West Nile virus, Measles virus, Mumps virus, Parainfluenza virus, Human metapneumovirus, Human papillomavirus, Rabies virus, Rubella virus, Human bocavirus, Parvovirus B19.

The immunogen can further be an immunogen from a pathogenic microorganism, including, without being limited to, *Rickettsia, Chlamydia, Mycobacteria, Clostridia, Corynebacteria, Mycoplasma, Ureaplasma, Legionella, Shigella, Salmonella, pathogenic Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4thed., Lippincott, N.Y., 1990, the entire contents of which are incorporated herein by reference for the teachings of pathogenic microorganisms).

The immunogen can further be an immunogen from pathogenic protozoa or pathogenic yeast and fungi.

The immunogen can also be an immunogen from chronic or latent infective agents, which typically persist because they fail to elicit a strong immune response in the subject. Illustrative latent or chronic infective agents include, but are not limited to, hepatitis B, hepatitis C, Epstein-Barr Virus, herpes viruses, human immunodeficiency virus, and human papilloma viruses.

Immunogens that are allergens are also contemplated by the present invention, which can include but are not limited to, environmental allergens such as dust mite allergens; plant allergens such as pollen, including ragweed pollen; insect allergens such as bee and ant venom; and animal allergens such as cat dander, dog dander and animal saliva allergens.

Accordingly, the compounds of formula (I) according to the invention and as described herein in the various embodiments may be used for allergy immunotherapy wherein the compound could be administered with together with the allergens to improve the development of tolerance, desensitization or immune deviation towards the allergen.

Further examples of allergens contemplated within the scope of the present invention are disclosed in WO 2006/085983 including ragweed allergen or grass allergen. Ragweed, and in particular Short Ragweed (*Ambrosia artemisiifolia*), is clinically the most important source of seasonal aeroallergens, as it is responsible for both the majority of cases and the most severe cases of allergic rhinitis (Pollart, et al. (1989) J. Allergy Clin. Immunol. 83(5):875-82; Rosenberg, et al. (1983) J. Allergy Clin. Immunol. 71(3):302-10; Bruce, et al. (1977) J. Allergy Clin. Immunol. 59(6): 449-59). Ragweed pollen also contributes significantly to exacerbation of asthma and allergic conjunctivitis.

Other exemplary food, animal, tree, insect and mold allergens are found at http://www.allergen.org/List.htm Marsh and Freidhoff. 1992. ALBE, an allergen database. (IUIS, Baltimore, Md. Edition 1.0).

The immunogen can further be an autoantigen (for example, to enhance self-tolerance to an autoantigen in a subject, e.g., a subject in whom self-tolerance is impaired). Examples of autoantigens contemplated within the scope of the present invention are disclosed in WO 2006/085983 including, without being limited to, actin, myelin basic protein, islet cell antigens, insulin, collagen and human collagen glycoprotein 39, muscle acetylcholine receptor and its separate polypeptide chains and peptide epitopes, glutamic acid decarboxylase and muscle-specific receptor tyrosine kinase, nicotinic acetylcholine receptor, transglutaminase, oxoglutarate dehydrogenase complex, branched-chain alpha-keto acid dehydrogenase complex, apolioprotein H, nucleoprotein 62, RA33, Sp100 nuclear antigen and nucleoporin 210 kDa.

The adjuvant according to the present invention represented by a compound of formula (I) as described herein in the various embodiments can be used for a variety of purposes and administered in various ways well known to those skilled in the art.

An exemplary disclosure of purposes and methods for administering an adjuvant is provided in WO 2006/085983. In particular, the adjuvant according to the invention may be used generally in active or passive immunization for producing antibodies in vivo or in vitro, or in methods of producing antibodies against an immunogen for any other purpose, e.g., for diagnostics or for use in histological techniques.

The adjuvant may further be used in human or veterinary therapy or prophylaxis. In particular, the adjuvant of the invention can be administered to a subject as a general immune enhancer to increase both innate and adaptive immune function in the subject, for example, in immunocompromised subjects such as subjects undergoing chemotherapy, radiation therapy, subjects with chronic infections (e.g., HCV and HBV) and/or subjects with HIV/AIDs. The invention can further be practiced to enhance the immune response to an attenuated live virus, a killed vaccine, or a DNA vaccine, all of which can have the disadvantage of reduced immunogenicity. The adjuvant of the invention can further be used to treat a chronic or latent infection to induce or enhance the immune response against the antigen(s) produced by the infection.

BRIEF DESCRIPTION OF THE FIGURES

FIG. 1: shows BALB/c mice which were administered with saline or sodium propionate (100 mg/kg) intranasally on days −3, −1, and 0. On day 0 all mice were infected with Influenza virus strain PR8. On day 5 post infection, mice were sacrificed, lungs isolated and viral load determined by PCR. Prophylactic treatment with sodium propionate administered intranasally resulted in a markedly lower viral load in the lungs of mice, as compared to mice treated with saline alone. These data show that sodium propionate exhibits efficacy in the protection against influenza virus infection when administered directly into the airways.

Figure 2:
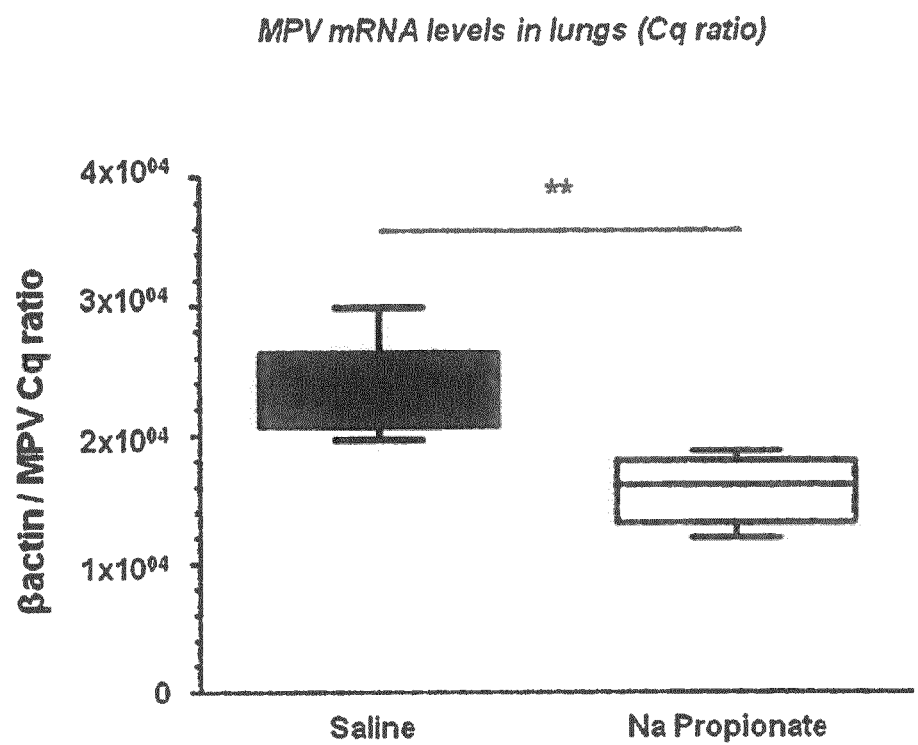

FIG. 2: shows BALB/c mice which were treated with saline or sodium propionate (100 mg/kg) intranasally on day −1 and 0. On Day 0 mice were infected with $1\times10^6$ PFU of Metapneumoia virus (MPV) A1 6621 intranasally and on day 5 post infection, mice were sacrificed, lungs removed and viral load determined by quantitative PCR. These data show that sodium propionate exhibits efficacy in the protection against MPV infection when administered directly into the airways.

FIGS. 3 A-D: show BALB/c mice which were treated with sodium propionate (100 mg/kg) or saline intranasally on day −5 and −3 (pretreatment group), or day −5, −3, 0, 2 and 4 (pretreatment and priming group), or day −5, −3, 0, 2, 4, 7, 9, 11 (pretreatment, priming and challenge group). On days 0, 2, 4, 7, 8 and 11 mice were exposed to 15 ug of house dust mite extract (Greer) intranasally. On day 14, all mice were sacrificed and bronchoalveolar lavage (BAL) was performed with sterile PBS. The total number of macrophages (FIG. 3B), eosinophils (FIG. 3A), lymphocytes (FIG. 3C) and neutrophils (FIG. 3D) was determined by total and differential cell counts using standard morphological and cytochemical techniques. The data show that all treatment regimes resulted in statistically significant reductions in airway eosinophilia indicative of a protective effect against the allergic response.

Figure 4:
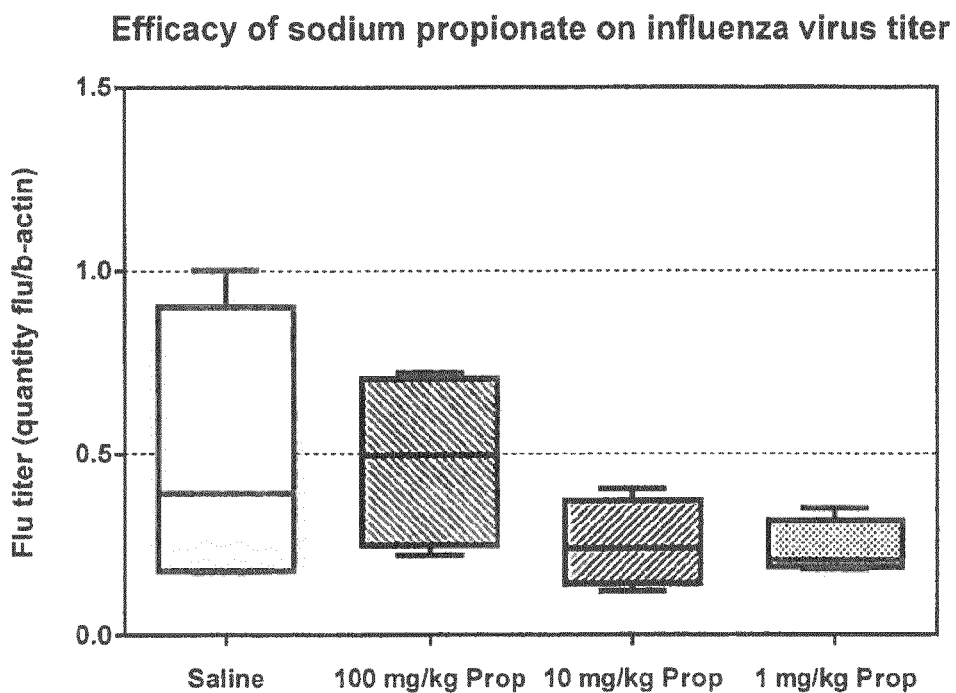

FIG. 4: shows BALB/c mice which were treated with saline or sodium propionate (100 mg/kg, 10 mg/kg, 1 mg/kg) intranasally on day 0. On day 0 all mice were infected with Influenza virus strain PR8. On day 5 post infection, mice were sacrificed, lungs isolated and viral load determined by PCR. All doses of sodium propionate yielded in a markedly lower viral load in the lungs of mice, as compared to mice treated with saline alone. These data show that a dose of 1 mg/kg sodium propionate administered intranasally on day 0 exhibits efficacy in the protection against influenza virus infection when administered directly into the airways.

Figure 5:
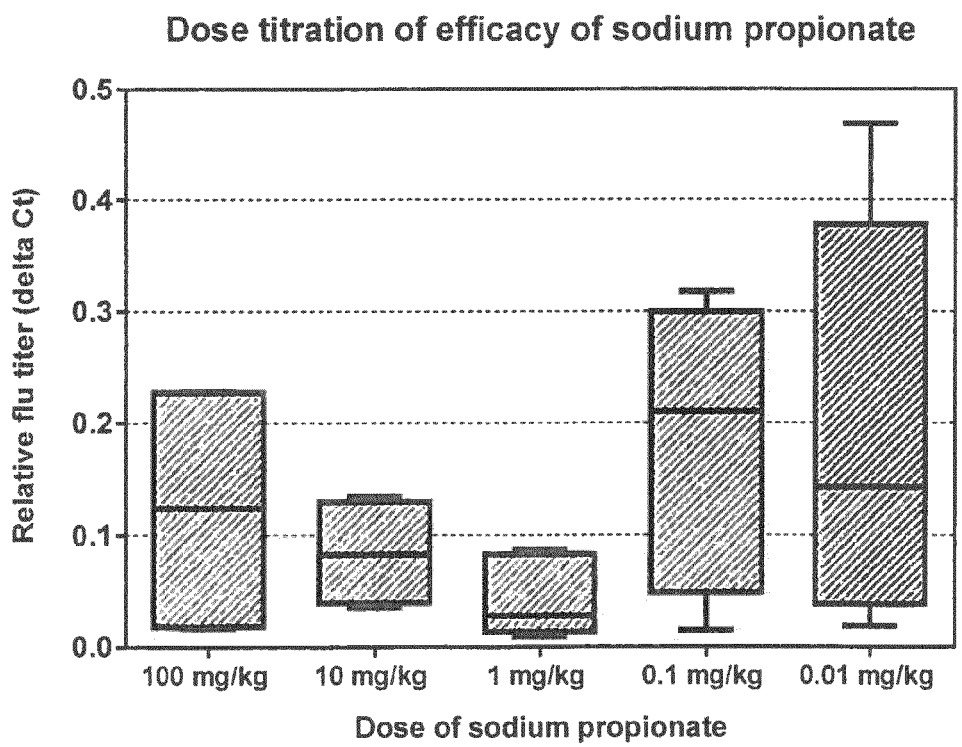

FIG. 5: shows BALB/c mice which were treated with sodium propionate (100 mg, 10 mg/kg, 1 mg/kg, 0.1 mg/kg, 0.01 mg/kg) intranasally on day 0. On day 0 all mice were infected with Influenza virus strain PR8. On day 5 post infection, mice were sacrificed, lungs isolated and viral load determined by PCR. A dose response effect of sodium propionate could be detected in the clearance of viral load in the lung tissue with a dose of 1 mg/kg showing the highest efficacy. These data show that a dose of 1 mg/kg sodium propionate administered intranasally on day 0 seems to be an optimal dose in the protection against influenza virus infection when administered directly into the airways.

Figure 6:
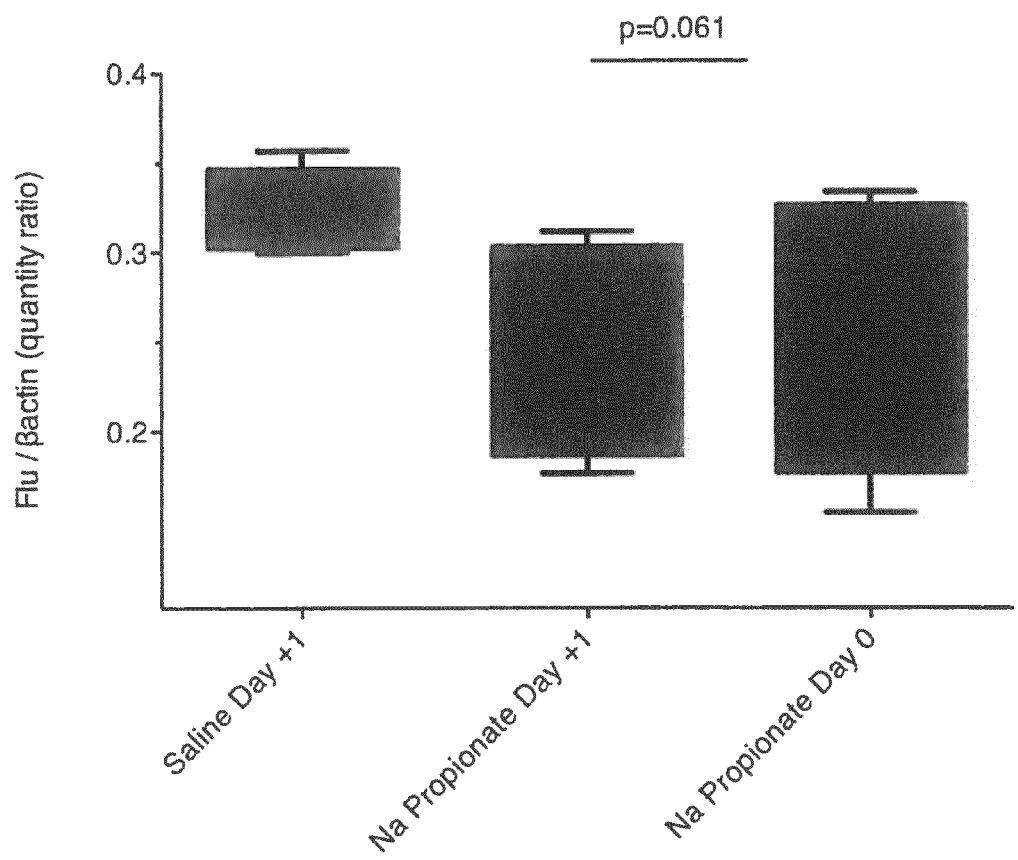

FIG. 6: show BALB/c mice, which were treated with saline or sodium propionate (100 mg/kg) intranasally on day 0 or day 1. On day 0 all mice were infected with Influenza virus strain PR8. On day 5 post infection, mice were sacrificed, lungs isolated and viral load determined by PCR. Efficacy in the reduction of viral load in the lung tissue on day 5 could be detected in animals treated with sodium propionate (100 mg/kg) intranasally on day 0 and on animals treated on day 1. These data show that a dose of 100 mg/kg sodium propionate administered intranasally on day 0 or day 1 exhibits efficacy in the protection against influenza virus infection when administered directly into the airways and as such that a therapeutic treatment regime of sodium propionate per nasal shows efficacy in reducing viral load.

EXAMPLES

Materials and Methods

The compounds of formula (I) can be manufactured by methods known in the art. Starting materials are either commercially available or can be prepared by methods known in the art.

Propionate: Sodium propionate can be obtained commercially or manufactured by methods known in the art.

Measurement of Antibodies:

Fel d 1-ELISA.

1. Coat flat bottom 96-well plate (NUNC-Immuno MaxiSorp) with 5 µg/ml Fel d 1 final in 100 µl/well using Carbonate buffer pH 9.6 (see recipe below).
2. Incubate overnight at 4° C.
3. Wash 4× with PBS/0.05% tween.
4. Block plate for 2 h at RT with 200 µl/well of PBS/0.05% Tween/1% BSA.
5. Make serial dilutions of your samples in PBS (usually 1:10, 1:100, 1:1000 and 1:10000 for sera and 1:10 and 1:100 for bronchial alveolar lavage fluid (BALE)).
6. Wash 4× with PBS/0.05% Tween,
7. Add 100 µl/well of diluted samples (in duplicates).
Note: Keep some wells to do test have a background control=blank (only PBS).
8. Incubate 2 h at RT.
9. Wash 4× with PBS/0.05% Tween.
10. Add 100 of Alkaline Phosphatase (AP)-conjugated anti-mouse IgG1, IgG2c, IgA or biotinylated anti-mouse IgE, all diluted at 1:1000 in PBS/0.2% BSA.
11. Incubate for 2 h at room temperature.
12. Wash 4× with PBS/0.05% Tween the wells with biotinylated anti-mouse IgE only and add 100 µl/well of AP-conjugated streptavidin diluted at 1:1000 in PBS/0.2% BSA.
13. Incubate 20 min at room temperature.
14. Wash 4× with PBS/0.05% Tween.
15. Dissolve 1 Alkaline Phosphatase Substrate Tablet (Sigma, cat. # N2765-100TAB) into 20 ml of TM Buffer.
16, Add 100 µl per well.
17. Develop in the dark and read at 405 nm.

Carbonate Buffer recipe: 8.4 g $NaHCO_3$, 3.56 g $Na_2CO_3$ qsp 1 Liter with $ddH_2O$. pH to 9.6 and store at 4° C.

TM Buffer recipe: 121.1 g Tris Base, 1 ml 0.3 M $MgCl_2$ qsp 1 Liter $ddH_2O$. pH to 9.8.

Cytokine and Chemokine Measurement: Bronchial alveolar lavage fluid was measured for specific cytokines utilizing a LegendPlex assay (Biolegend) following manufacturers instructions.

Collection and Analysis of Bronchoalveolar Lavage (BAL) Cells.

BAL was performed by flushing the airways three times with 1 ml PBS. Total BAL cells were counted using a Coulter Counter (IG Instruments) and spun onto glass slides using a Cytospin 2 (Shandon Southern Products, Ltd.). Cells were then stained with Diff Quick staining set (Siemens-Dade Behring). Percentages of eosinophils, macrophages, lymphocytes and neutrophils were determined microscopically using standard morphological and cytochemical criteria.

Example 1

Propionate Intranasal Efficacy Study—Influenza

Female BALB/c mice were purchased from Charles River Laboratories at 8 weeks of age. The mice were exposed to either 30 µl of sterile saline or 30 µl of Sodium Propionate dissolved in saline (100 mg/kg dose) intranasally on day −3, −1 and 0. On day 0 mice were infected with 100 PFU of Influenza strain PR8 in 30 µl of PBS solution. On day 5 post infection, mice were sacrificed and lungs were removed and placed in Tri reagent solution. Total RNA was purified from cells obtained from whole lung tissue using Tri reagent. Real time PCR was carried out according to manufacturers instructions using the quantifast SYBR green RT-PCR kit (Qiagen). The following primers influenza matrix protein primers were used: forward 5'-GGA CTG CAG CGT AGA CGC TT-3', reverse 5'-CAT CCT GTT GTA TAT GAG GCC CAT-3'. B-actin primers forward 5'-CCC TGA AGT ACC CCA TTG AAC-3', reverse 5'-CTT TTC ACG GTT GGC CTT AG-3' as previously described van Elden, L. J., M. Nijhuis, P. Schipper, R. Schuurman, A. M. van Loon. 2001. Simultaneous detection of influenza viruses A and B using real-time quantitative PCR. *J. Clin. Microbial.* 39: 196-200. Prophylactic treatment with sodium propionate administered intranasally resulted in a markedly lower viral load in the lungs of mice, as compared to mice treated with saline alone. These data show that sodium propionate exhibits efficacy in the protection against influenza virus infection when administered directly into the airways (as shown in FIG. 1).

Example 2

Propionate is Effective Against Metapneumonia Virus (MPV)

Female BALB/c mice (10 weeks old, Charles River Laboratories) were given Sodium Propionate (100 mg/kg) or saline intranasally in a volume of 30 ul on day −1 and 0. On day 0 mice were infected with 1×10⁶ PFU of metapneumonia virus A1 6621 (MPV) in a volume of 100 ul.

On day 5 post infection, mice were sacrificed and lungs were removed and placed in Tri reagent solution. Total RNA was purified from cells obtained from whole lung tissue using Tri reagent. Real time PCR was carried out according to manufacturers instructions using the quantifast SYBR green RT-PCR kit (Qiagen). The following primers MPV-specific primers were used: forward 5'-GCC GTT AGC TTC AGT CAA TTC AA-3', reverse 5'-TCC AGC ATT GTC TGA AAA TTG C-3'. B-actin primers forward 5'-CCC TGA AGT ACC CCA TTG AAC-3', reverse 5'-CTT TTC ACG GTT GGC CTT AG-3'. These data show that sodium propionate exhibits efficacy in the protection against MPV infection when administered directly into the airways (as shown in FIG. 2 and Table 1).

TABLE 1

Propionate exhibits efficacy in the protection against MPV infection.

| Mouse Number | Saline (Control) [β-actin/MPV Cq ratio] | Na Propionate [β-actin/MPV Cq ratio] |
| --- | --- | --- |
| 1 | 21000 | 17300 |
| 2 | 19700 | 16200 |
| 3 | 29900 | 14500 |
| 4 | 25100 | 12000 |
| 5 | 25200 | 18800 |
| 6 | 24300 | |

Example 3

Propionate Intranasal Efficacy Study—HDM Asthma

Female BALB/c mice were purchased from Charles River Laboratories at 8 weeks of age. On day −5 and −3 (pretreatment group), or day −5, −3, 0, 2 and 4 (pretreatment and priming group), or day −5, −3, 0, 2, 4, 7, 9, 11 (pretreatment, priming and challenge group) mice were exposed to sterile saline or sodium propionate (100 mg/kg) intranasally in 15 µl of solution. On days 0, 2, 4, 7, 8 and 11 mice were exposed to 15 µg of house dust mite extract (Greer) per nasal. On day 14, all mice were sacrificed and bronchoalveolar lavage (BAL) was performed with sterile PBS. The total number of macrophages, eosinophils, lymphocytes and neutrophils was determined by total and differential cell counts using standard morphological and cytochemical techniques. Specifically, total cell count was performed using a coulter Z2® (Particle count and size analyzer, Beckman coulter). Cytospin preparations of 50,000 cells were performed at 800 rpm for 5 min (Cytospin 3e, Thermo Shandon, Astmoor, United Kingdom). After cytocentrifugation, cells were stained using Diff-Quick kit (IMEB, Chicago, Ill.), and differential cell counts obtained using standard morphological criteria to classify individual leukocyte populations. The data show that all treatment regimes resulted in statistically significant reductions in airway eosinophilia indicative of a protective effect against the allergic response (as shown in FIGS. 3A-D).

Example 4

Efficacy of Short Chain Fatty Acids Against Influenza Virus Infection in Mice

Sodium propionate given into the airways of BALB/c mice is protective against influenza infection. Its effective range was shown to be in a range of between 100 mg/kg and 1 mg/kg.

4.1 Experiment 1: Effectiveness of pretreatment of mice with sodium propionate i.n. (at indicated doses) on protection against influenza virus 4.1.1 Material and Methods 4.1.1.1 Number of Animals:

Four female BALB/c mice aged 8 weeks (purchased from Charles River) were used per group.

4.1.1.2 Preparation of Dose Formulation:

Sodium propionate was dissolved in the balanced salt solution phosphate buffered saline (PBS) at a concentration of either 40 mg/ml (for 100 mg/kg dosing); 4.0 mg/ml (for 10 mg/kg dosing) or 0.4 mg/ml (for 1 mg/kg dosing). The solutions were filter-sterilized using 0.2 syringe filters and stored at 4° C. PBS alone was used as a control.

4.1.1.3 Intranasal/Nasal Administration (i.n.):

On day 0 mice were anaesthetized by intraperitoneal (i.p.) injection with ketamine/xylazine and then 50 µl of the indicated solutions were administered utilizing a 200 µl pipette into the nostrils. The solutions were all rapidly inhaled by the anaesthetized animals.

4.1.1.4 Influenza Infection:

On day 0, four hours following the administration of the propionate solutions or control solution, mice were anaesthetized as described before and infected with 100 PFU of Influenza A strain HK/PR8 per nasal.

4.1.1.5 Viral Titer Analysis:

The viral titers in the lungs were determined five days post infection (known to be the peak of the viral load in the lung from previous studies). For this analysis, the mice were euthanized by i.p. injection of 150 mg/kg, pentobarbital in 200 µl volume. Lungs were removed en bloc under sterile conditions, placed in Tri reagent and RNA was isolated following the manufacturers instructions (Molecular Research).

Real time PCR was carried out according to manufacturers instructions using the quantifast SYBR green RT-PCR kit (Qiagen). The following primers were used: GAPDH forward 5'-GGGTGTGAACCACGAGAAAT-3'; GAPDH reverse 5'-CCTTCCACAATGCCAAAGTT-3'; Influenza matrix protein forward 5'-GGA CTG CAG CGT AGA CCC TT-3', reverse 5'-CAT CCT GTT GTA TAT GAG GCC CAT-3'. Expression was determined either by using absolute quantification or by comparative delta threshold cycle method using GAPDH as a comparator.

4.1.2 Result:

As shown in FIG. 4 and Table 2 below, mice treated with 1-100 mg/kg of sodium propionate revealed reduced Flu titers compared to mice that only received saline (control). The lowest Flu titers could be observed in mice which received 1 mg/kg.

TABLE 2

Mice treated with propionate show reduced Flu titers compared to control mice which received only saline.

| Mouse number | Saline (control) | 100 mg/kg Na Propionate [flu/β-actin] | 10 mg/kg Na Propionate [flu/β-actin] | 1 mg/kg Na Propionate [flu/β-actin] |
|---|---|---|---|---|
| 1 | 0.1739915 | 0.6613417 | 0.2044192 | 0.2110155 |
| 2 | 0.5965181 | 0.7202522 | 0.1213331 | 0.2010858 |
| 3 | 1.001817 | 0.2205769 | 0.4034525 | 0.3507077 |
| 4 | 0.1876335 | 0.3315154 | 0.2733269 | 0.1830315 |

4.2 Experiment 2: Intranasal dose titration of sodium propionate for treatment of influenza infection 4.2.1 Material and Methods The Material and Methods of Experiment 1 have been used, as described in section 4.1.1 above.

4.2.2 Result:

As depicted in FIG. 5 and Table 3 below, the dose titration of intranasally administered sodium propionate against influenza infection shows a trend towards efficacy from 100 mg/kg to 1 mg/kg and lack of efficacy at a dose of 0.1 mg/kg or less. Mice which received 1 mg/kg sodium propionate showed the lowest Flu titer. From this results it can be concluded, that the intranasal administration of sodium propionate at a dose of about 1 mg/kg may exhibit an ancillary effect if administered together with a balanced saline solution for the treatment of common cold and acute rhinitis.

TABLE 3

Dose titration of intranasally administered sodium propionate against influenza infection.

| mouse number | 100 mg/kg Na Propionate [delta Ct] | 10 mg/kg Na Propionate [delta Ct] | 1 mg/kg NA Propionate [delta Ct] | 0.1 mg/kg NA Propionate [delta Ct] | 0.01 mg/kg NA Propionate [delta Ct] |
|---|---|---|---|---|---|
| 1 | 0.2248162 | 0.05122631 | 0.00903277 | 0.01483913 | 0.01898603 |
| 2 | 0.2282335 | 0.1345269 | 0.07967126 | 0.2815218 | 0.2874926 |
| 3 | 0.02337933 | 0.1146394 | 0.01818559 | 0.3177531 | 0.05776232 |
| 4 | 0.01681005 | 0.03546309 | 0.02787356 | 0.082389 | 0.1427489 |
| 5 | | | 0.086991 | 0.2101459 | 0.468696 |

The working hypothesis for this ancillary effect is that sodium propionate supports a rebalancing of the local immune defense mechanisms in the nasal mucosa (NALT system) and facilitates on this way the main efficacy of administration of the saline solution for the regularization of the mucociliary defense system against pathogens. It could be demonstrated that intranasal administered sodium propionate has a protective efficacy against virus infection in mice at much lower doses compared to the systemic administration (e.g. oral or intraperitoneal administration). Sodium propionate has in principle a therapeutic efficacy against influenza virus if it is administered systemically in very high doses of about 1 g/kg body weight. This dose corresponds to a daily dose of 60 g sodium propionate for a patient, which is practically not feasible. Furthermore interferences and disturbances in the regular metabolic pathways should be expected as negative side effects. According to the results demonstrated above a dose of 1 mg/kg sodium propionate is an optimal dose for the intended treatment. This dose corresponds to a daily dose of 60 mg per human being/consumer/patient. The solubility of sodium propionate in water is specified as 100 mg/mL. The maximal dosing volume for one pump action of the 3K-system is 140 mg. Considering the solubility this amount contains 14 mg of sodium propionate which will be administered by one pump action. Conclusively two pump action per nostril are necessary to administer 28 mg and if both nostrils are used the dose which is relevant for the ancillary effect of sodium propionate can be achieved.

4.2.3 Mechanism of Action

The mucociliary system in the nasal cavities is the first line of defence against pathogens like viruses or bacteria which are coming into the human body by the upper airways. The first and mandatory prerequisite for an effective functionality of this defence mechanism is a moist environment for the mucosa.

The second line of defense against the invasion of pathogens is the specific local immune system in nasal respiratory mucosa which is part of the general lymphatic system (mucosa-associated lymphatic tissue; MALT) and specified as NALT (nose-associated lymphatic tissue).

In case of pathogen invasion, multiple immunocompetent cells immigrate, and increase the importance and functionality of this cellular defense mechanism. Up to now, no efficient treatment regimens exist, which are supporting this local immune system in the respiratory mucosa without generating undesired systemic side effects. Thus, the present invention provides novel means and methods to modulate and induce the specific local immune system in nasal respiratory mucosa towards a Th1 cell response by transmucosal administration of SCFA, particularly administration of intranasal administration of propionic acid or a pharmaceutically acceptable salt thereof.

4.3 Experiment 3: Determination of efficacy dependent from timing of treatment 4.3.1 Material and Methods The Material and Methods of Experiment 1 have been used, which are found under 4.1.1.

4.3.2 Result:

As shown in FIG. 6 and Table 4 below, sodium propionate can be given before infection, the day of infection or the day after influenza infection with similar efficacy. The treatment with sodium propionate i.n. (100 mg/kg) one day after influenza infection (Day +1) is still as effective against controlling the virus as a treatment at the day of infection (Day 0).

TABLE 4

Timing of treatment of influenza infection.

| mouse number | Saline Day +1 [flu/β-actin] | Na Propionate Day +1 [flu/β-actin] | Na Propionate Day 0 [flu/β-actin] |
| --- | --- | --- | --- |
| 1 | 0.316 | 0.277 | 0.244 |
| 2 | 0.3 | 0.312 | 0.334 |
| 3 | 0.311 | 0.217 | 0.303 |
| 4 | 0.357 | 0.176 | 0.154 |

The invention claimed is:

1. A composition comprising a compound according to formula (I)

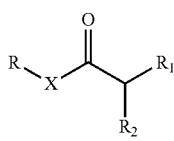

wherein

X is —O—,

R is selected from the group consisting of methyl, ethyl, propyl, benzyl, nitrobenzyl, and polyethylene glycol;

$R_1$ selected from the group consisting of ethyl, hydroxyethyl; and $R_2$ is hydrogen;

or pharmaceutical acceptable salts thereof, in a pharmaceutically effective amount, together with a pharmaceutically acceptable carrier and/or a balanced salt solution formulated as an aerosol; a dry powder or a liquid preparation for intranasal administration.

2. A pharmaceutical kit comprising the composition of claim 1 in a separate unit dosage form suitable for delivery with a nasal insufflator device.

3. The composition of claim 1, wherein R1 is ethyl and R is selected from the group consisting of methyl, ethyl, proplyl, benzyl, nitrobenzyl, and polyethylene glycol.

4. The composition of claim 1, wherein R1 is hydroxyethyl, and R is selected from the group consisting of methyl, ethyl, propyl, benzyl, nitrobenzyl, and polyethylene glycol.

5. The composition of claim 1, wherein R is methyl.
6. The composition of claim 1, wherein R is ethyl.
7. The composition of claim 1, wherein R is propyl.
8. The composition of claim 1, wherein R is benzyl.
9. The composition of claim 1, wherein R is nitrobenzyl.
10. The composition of claim 1, wherein R is polyethylene glycol.
11. The pharmaceutical composition of claim 2, wherein the composition is provided in unit dosage form in a nasal insufflator device.

* * * * *